(12) United States Patent
Keeler et al.

(10) Patent No.: US 10,987,167 B2
(45) Date of Patent: Apr. 27, 2021

(54) BIASING LASER CATHETER: MONORAIL DESIGN

(71) Applicant: The Spectranetics Corporation, Colorado Springs, CO (US)

(72) Inventors: Jacob Keeler, Colorado Springs, CO (US); Melissa Brookshier, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 105 days.

(21) Appl. No.: 14/152,334

(22) Filed: Jan. 10, 2014

(65) Prior Publication Data

US 2014/0194861 A1 Jul. 10, 2014

Related U.S. Application Data

(63) Continuation of application No. 12/265,441, filed on Nov. 5, 2008, now abandoned.

(51) Int. Cl.
*A61B 18/24* (2006.01)
*A61B 18/22* (2006.01)
*A61B 17/22* (2006.01)

(52) U.S. Cl.
CPC .. *A61B 18/245* (2013.01); *A61B 2017/22038* (2013.01); *A61B 2018/2238* (2013.01)

(58) Field of Classification Search
CPC .. A61B 18/24; A61B 18/245; A61B 2018/225

(Continued)

(56) References Cited

U.S. PATENT DOCUMENTS 4,053,845 A 10/1977 Gould
4,445,892 A 5/1984 Hussein et al.
(Continued)

FOREIGN PATENT DOCUMENTS

EP 0165301 B1 4/1991
EP 2015672 B1 1/2009
(Continued)

OTHER PUBLICATIONS

Extended Search Report for European Patent Application No. 09833795.9 dated Apr. 12, 2012 6 pages.
(Continued)

*Primary Examiner* — John R Downey

(57) ABSTRACT

In some embodiments, without limitation, the invention comprises a catheter having an elongated housing with a channel disposed therein. A laser delivery member is movable and at least partially disposed within the channel. A ramp is disposed within the housing at an angle to its central axis and proximate to its distal end. The ramp is adapted to move the distal end of the laser delivery member outwardly from the central axis of the housing. A guidewire biases the distal end of the laser delivery member generally inwardly toward the central axis of the housing. In some embodiments, without limitation, the offset of the central axis of the tip of the laser delivery member from the central axis of the housing is determined by adjusting the extent to which the laser delivery member travels on the ramp, and disposition of the laser delivery member on the guidewire maintains the offset tip substantially parallel to the central axis of the housing. Thus, in accordance with the invention, the distal end of the laser delivery member may be biased in a desired direction or offset, permitting ablation of an area larger than the area of the distal end of the catheter.

8 Claims, 19 Drawing Sheets

(58) Field of Classification Search
USPC .................................................. 606/14, 15
See application file for complete search history.

(56) References Cited

U.S. PATENT DOCUMENTS

| | | | |
|---|---|---|---|
| 4,641,912 A | 2/1987 | Goldenberg | |
| 4,669,467 A | 6/1987 | Willett et al. | |
| 4,686,979 A | 8/1987 | Gruen et al. | |
| 4,732,448 A | 3/1988 | Goldenberg | |
| 4,747,405 A | 5/1988 | Leckrone | |
| 4,784,132 A | 11/1988 | Fox et al. | |
| 4,799,754 A | 1/1989 | Goldenberg | |
| 4,807,620 A | 2/1989 | Strul et al. | |
| 4,830,460 A | 5/1989 | Goldenberg | |
| 4,844,062 A | 7/1989 | Wells | |
| 4,848,336 A | 7/1989 | Fox et al. | |
| 4,886,496 A | 12/1989 | Conoscenti et al. | |
| 4,924,863 A | 5/1990 | Sterzer | |
| 5,016,964 A | 5/1991 | Donnelly | |
| 5,040,548 A | 8/1991 | Yock | |
| 5,041,108 A | 8/1991 | Fox et al. | |
| 5,042,976 A | 8/1991 | Ishitsu et al. | |
| 5,188,632 A | 2/1993 | Goldenberg | |
| 5,222,945 A * | 6/1993 | Basnight | A61M 5/3271 604/110 |
| 5,250,045 A | 10/1993 | Bohley | |
| 5,263,952 A | 11/1993 | Grace et al. | |
| 5,263,953 A | 11/1993 | Bagby | |
| 5,267,994 A * | 12/1993 | Gentelia | A61B 18/1482 604/35 |
| 5,300,085 A | 4/1994 | Yock | |
| 5,304,171 A | 4/1994 | Gregory et al. | |
| 5,350,375 A | 9/1994 | Deckelbaum et al. | |
| 5,350,395 A | 9/1994 | Yock | |
| 5,352,197 A | 10/1994 | Hammersmark et al. | |
| 5,354,295 A * | 10/1994 | Guglielmi | A61B 17/12022 606/32 |
| 5,415,653 A | 5/1995 | Wardle et al. | |
| 5,429,604 A | 7/1995 | Hammersmark et al. | |
| 5,429,617 A | 7/1995 | Hammersmark et al. | |
| 5,449,354 A * | 9/1995 | Konwitz | A61B 18/24 606/13 |
| 5,451,233 A | 9/1995 | Yock | |
| 5,456,680 A | 10/1995 | Taylor et al. | |
| 5,514,128 A | 5/1996 | Hillsman et al. | |
| 5,531,708 A * | 7/1996 | Woodruff | A61M 5/31555 604/208 |
| 5,571,151 A | 11/1996 | Gregory | |
| 5,573,531 A | 11/1996 | Gregory | |
| 5,593,402 A * | 1/1997 | Patrick | A61B 17/29 604/902 |
| 5,623,940 A | 4/1997 | Daikuzono | |
| 5,643,251 A | 7/1997 | Hillsman et al. | |
| 5,649,923 A | 7/1997 | Gregory et al. | |
| 5,685,864 A * | 11/1997 | Shanley | A61M 5/31586 604/187 |
| 5,722,972 A | 3/1998 | Power et al. | |
| 5,817,144 A | 10/1998 | Gregory | |
| 5,824,026 A | 10/1998 | Diaz | |
| 5,836,941 A * | 11/1998 | Yoshihara | A61B 18/24 606/15 |
| 5,836,946 A | 11/1998 | Diaz et al. | |
| RE36,104 E | 2/1999 | Solar | |
| 5,976,124 A | 11/1999 | Reiser | |
| 5,989,243 A | 11/1999 | Goldenberg | |
| 6,022,342 A | 2/2000 | Mukherjee | |
| 6,027,460 A | 2/2000 | Shturman | |
| 6,036,715 A | 3/2000 | Yock | |
| 6,066,130 A | 5/2000 | Gregory et al. | |
| 6,090,118 A | 7/2000 | McGuckin et al. | |
| 6,117,128 A | 9/2000 | Gregory | |
| 6,290,668 B1 | 9/2001 | Gregory et al. | |
| 6,458,098 B1 | 10/2002 | Kanesaka | |
| 6,575,993 B1 | 6/2003 | Yock | |
| 6,602,264 B1 | 8/2003 | McGuckin et al. | |
| 6,613,038 B2 | 9/2003 | Bonutti et al. | |
| 6,669,667 B1 * | 12/2003 | Yang | A61M 5/322 604/110 |
| 6,743,208 B1 | 6/2004 | Coyle | |
| 6,824,550 B1 | 11/2004 | Noriega et al. | |
| 6,872,206 B2 | 3/2005 | Edwards et al. | |
| 7,037,316 B2 | 5/2006 | McGuckin et al. | |
| 7,090,683 B2 | 8/2006 | Brock et al. | |
| 7,169,141 B2 | 1/2007 | Brock et al. | |
| 7,214,230 B2 | 5/2007 | Brock et al. | |
| 7,252,664 B2 | 8/2007 | Nasab et al. | |
| 7,329,223 B1 | 2/2008 | Ainsworth et al. | |
| 7,371,210 B2 | 5/2008 | Brock et al. | |
| 7,507,246 B2 | 3/2009 | McGuckin et al. | |
| 7,628,763 B2 | 12/2009 | Noriega et al. | |
| 7,674,253 B2 | 3/2010 | Fisher et al. | |
| 7,744,608 B2 | 6/2010 | Lee et al. | |
| 7,758,569 B2 | 7/2010 | Brock | |
| 7,789,875 B2 | 9/2010 | Brock et al. | |
| 7,930,065 B2 | 4/2011 | Larkin et al. | |
| 8,043,314 B2 | 10/2011 | Noriega et al. | |
| 8,052,704 B2 | 11/2011 | Olson | |
| RE43,328 E | 4/2012 | Foley et al. | |
| 8,353,922 B2 | 1/2013 | Noriega et al. | |
| 8,409,136 B2 | 4/2013 | Wallace et al. | |
| 8,414,505 B1 | 4/2013 | Weitzner et al. | |
| 8,469,979 B2 | 6/2013 | Olson | |
| 8,496,680 B2 | 7/2013 | Noriega et al. | |
| 8,641,705 B2 | 2/2014 | Leo et al. | |
| 8,684,952 B2 | 4/2014 | Weitzner et al. | |
| 8,747,332 B2 | 6/2014 | Noriega et al. | |
| 8,821,483 B2 | 9/2014 | Boutoussov et al. | |
| 8,920,402 B2 | 12/2014 | Nash et al. | |
| RE45,484 E | 4/2015 | Foley et al. | |
| 9,028,489 B2 | 5/2015 | Choi | |
| 9,028,499 B2 | 5/2015 | Keyak et al. | |
| 9,060,793 B2 | 6/2015 | Larkin et al. | |
| 9,066,742 B2 | 6/2015 | Splinter | |
| 9,084,623 B2 | 7/2015 | Gomez et al. | |
| 9,084,624 B2 | 7/2015 | Larkin et al. | |
| 9,095,681 B2 | 8/2015 | Wenderow et al. | |
| 9,101,380 B2 | 8/2015 | Larkin et al. | |
| 9,113,955 B2 | 8/2015 | Noriega et al. | |
| 9,119,609 B2 | 9/2015 | O'Sullivan et al. | |
| 9,125,562 B2 | 9/2015 | Spencer et al. | |
| 9,125,679 B2 | 9/2015 | Larkin et al. | |
| 9,168,356 B2 | 10/2015 | Wenderow et al. | |
| 9,173,713 B2 | 11/2015 | Hart et al. | |
| 9,237,920 B2 | 1/2016 | Leo et al. | |
| 9,241,733 B2 | 1/2016 | Olson | |
| 9,254,143 B2 | 2/2016 | Huynh et al. | |
| 9,261,259 B2 | 2/2016 | Shiomi et al. | |
| 9,289,173 B2 | 3/2016 | Splinter | |
| 9,289,258 B2 | 3/2016 | Cohen | |
| 9,351,726 B2 | 5/2016 | Leimbach et al. | |
| 9,351,727 B2 | 5/2016 | Leimbach et al. | |
| 9,351,789 B2 | 5/2016 | Novichenok et al. | |
| 2002/0151879 A1 | 10/2002 | Loeb | |
| 2003/0055398 A1 * | 3/2003 | Imran | A61B 17/22 604/510 |
| 2004/0015159 A1 | 1/2004 | Slater et al. | |
| 2006/0167442 A1 * | 7/2006 | Hebert | A61B 18/24 606/14 |
| 2006/0206182 A1 | 9/2006 | Pyles | |
| 2007/0270787 A1 | 11/2007 | Winston et al. | |
| 2007/0299496 A1 | 12/2007 | Podmore et al. | |
| 2008/0009673 A1 | 1/2008 | Khachi | |
| 2008/0098564 A1 * | 5/2008 | Fojtik | A61M 5/31511 16/221 |
| 2008/0154213 A1 * | 6/2008 | Kiehne | A61M 5/31501 604/220 |
| 2008/0154354 A1 | 6/2008 | Taylor | |
| 2008/0249515 A1 | 10/2008 | Taylor | |
| 2009/0105686 A1 | 4/2009 | Snow et al. | |
| 2010/0114081 A1 | 5/2010 | Keeler et al. | |
| 2011/0292378 A1 | 12/2011 | Brown | |
| 2011/0319885 A1 | 12/2011 | Skwarek et al. | |
| 2013/0096545 A1 | 4/2013 | Laudenslager et al. | |
| 2013/0289672 A1 | 10/2013 | Hakomori et al. | |

(56) References Cited

U.S. PATENT DOCUMENTS

| | | |
|---|---|---|
| 2014/0031800 A1 | 1/2014 | Ben Oren et al. |
| 2014/0276594 A1 | 9/2014 | Tanner et al. |
| 2015/0150587 A1 | 6/2015 | Smith et al. |
| 2015/0272664 A9 | 10/2015 | Cohen |
| 2015/0342681 A1 | 12/2015 | Lee |
| 2015/0349480 A1 | 12/2015 | Hongo et al. |
| 2015/0359594 A1 | 12/2015 | Ben-Oren et al. |
| 2015/0359595 A1 | 12/2015 | Ben Oren et al. |
| 2016/0120603 A1 | 5/2016 | Grace et al. |
| 2016/0151606 A9 | 6/2016 | Weitzner et al. |
| 2016/0183844 A1 | 6/2016 | Splinter |
| 2016/0184020 A1 | 6/2016 | Kowalewski et al. |
| 2016/0192936 A1 | 7/2016 | Leimbach et al. |
| 2016/0220300 A1 | 8/2016 | Cohen |

FOREIGN PATENT DOCUMENTS

| | | |
|---|---|---|
| EP | 2282803 B1 | 2/2011 |
| WO | 2014118738 A1 | 8/2014 |
| WO | 2014158688 A1 | 10/2014 |
| WO | 2014182946 A2 | 11/2014 |
| WO | 2015089377 A1 | 6/2015 |
| WO | 2015159296 A1 | 10/2015 |
| WO | 2016069754 A1 | 5/2016 |

OTHER PUBLICATIONS

International Preliminary Report on Patentability for International Patent Application No. PCT/US2009/065557, dated Jun. 30, 2011, 6 Pages.

International Search Report and Written Opinion issued in PCT/US2009/065557 dated Jan. 26, 2010, 12 pages.

Official Action for European Patent Application No. 09833795.9 dated Nov. 20, 2012, 4 pages.

International Search Report and Written Opinion issued in PCT/US2015/057834, dated Jan. 26, 2016, 11 pages.

* cited by examiner

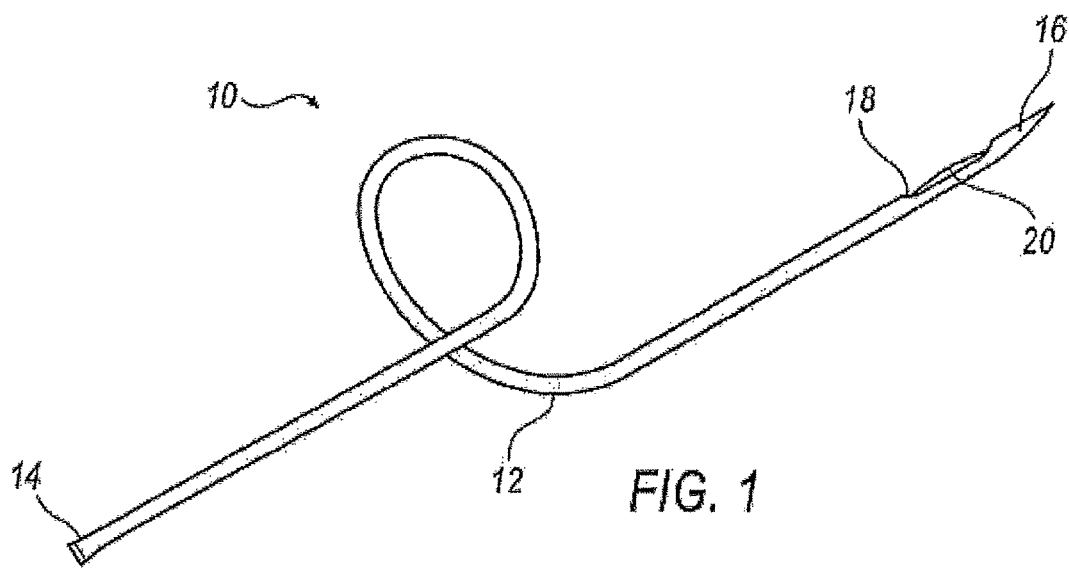
FIG. 1
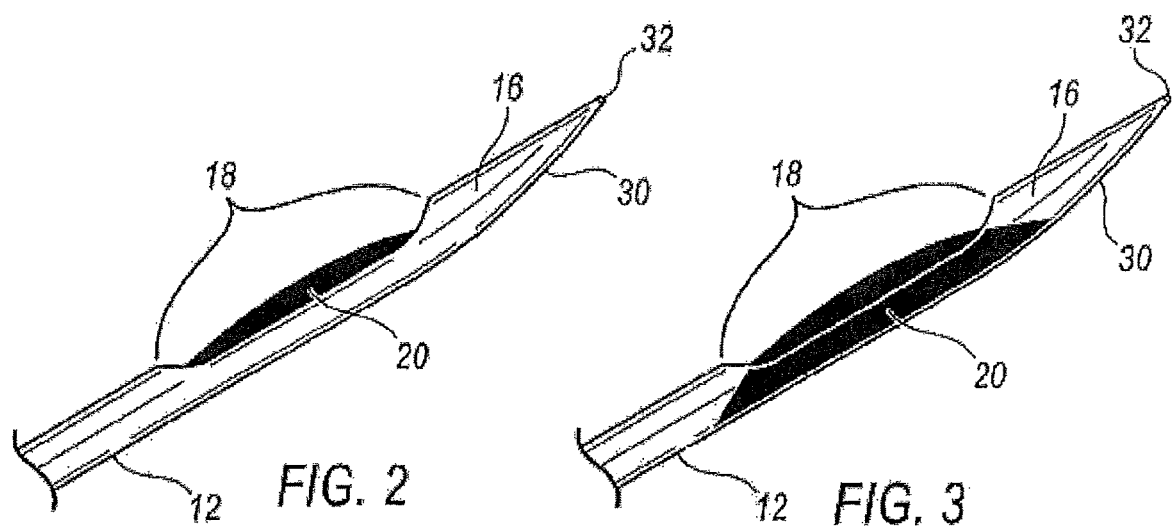
FIG. 2
FIG. 3
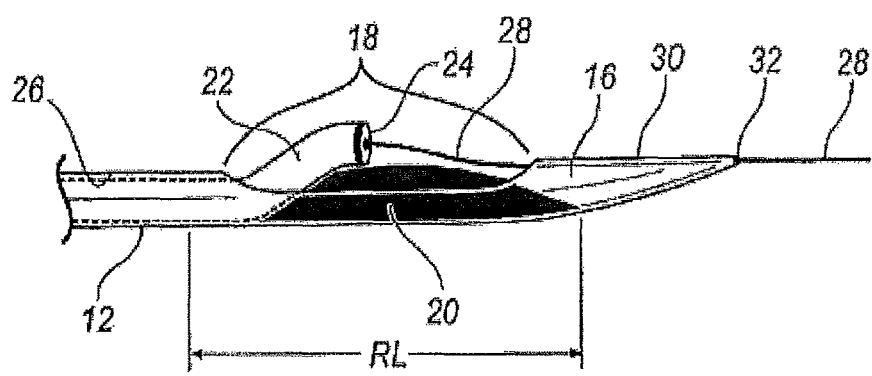
FIG. 4

BIASING LASER CATHETER: MONORAIL DESIGN

TECHNICAL FIELD

The embodiments described herein are generally directed to improved apparatus and methods for the delivery of laser energy, including without limitation, to a laser delivery catheter.

BACKGROUND OF THE INVENTION

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up angioplasty is recommended.

Thus, it would be desirable to provide an apparatus and methods that could bias the distal end of the laser catheter in a desired direction to enable the clinician to ablate an area larger than the area of the distal end of the catheter. Furthermore, because plaque may be eccentric in a blood vessel and require directional control to adequately ablate the target area, it would be advantageous to provide an apparatus that is sufficiently flexible to travel and rotate around the target area so that the clinician may control the area to be ablated.

BRIEF SUMMARY OF THE INVENTION

In accordance with some embodiments, without limitation, a catheter is provided having an elongated housing, a laser delivery member, a cavity disposed within the elongated housing, a ramp disposed within the cavity, a slot disposed within the elongated housing, and a guidewire. The elongated housing may have a central axis between a first proximal end and a first distal end and/or may have a channel disposed between the first proximal end and the first distal end. The laser delivery member may have a second proximal end, a second distal end, and at least one optical fiber. The laser delivery member may be at least partially disposed within the channel and movable therein. The cavity may be disposed proximate the first distal end of the elongated housing and/or may be in mechanical communication with the channel. The ramp may be disposed at an angle to the central axis and proximate the first distal end of the elongated housing. The ramp may be in mechanical communication with the channel. The ramp may also be adapted to move the second distal end of the laser delivery member outwardly from the central axis of the elongated member. The guidewire may be in mechanical communication with both the laser delivery member and the elongated housing. The guidewire may be adapted to bias the second distal end of the laser delivery member generally inwardly toward the central axis. The slot may disposed proximal to the cavity and may be in mechanical communication with the channel and the cavity. The slot may be configured to permit a portion of the guidewire to move from within the channel outwardly from the central axis of the elongated housing when the second distal end of the laser delivery member moves outwardly from the central axis of the elongated member when engaged with the ramp.

In some embodiments, the guidewire may be at least partially eccentrically disposed within the laser delivery member. In other embodiments, a trigger in mechanical communication with the laser delivery member and the elongated housing may be include. The trigger may be configured to actuate the laser delivery member relative to the elongated housing. The trigger may actuate the laser delivery member relative to the elongated housing in response to trigger actuation. For example, the trigger may actuate the laser delivery member from a first position relative to the elongated housing to a second position relative to the elongated housing. In some examples, the laser delivery member may be at least partially disposed within the cavity in the first position and may be at least partially disposed external to the cavity in the second position.

In accordance with some embodiments, without limitation, a catheter is provided having an elongated housing, a light guide, a guidewire, and a monorail. The elongated housing may have a central axis, a distal end, a proximal end and a housing channel disposed between the distal end and the proximal end. The light guide may have a distal end and a proximal end. The guidewire may be at least partially disposed within the housing channel and in mechanical communication with the light guide and the elongated housing. The monorail may be an attachment or may be integrally coupled with the elongated housing. The monorail may also have a central axis substantially parallel with the central axis of the elongated housing. In some embodiments, the monorail may also include: a monorail proximal end coupled with the distal end of the elongated housing; a monorail distal end; a monorail channel in mechanical communication with the housing channel and extending from the monorail proximal end to the monorail distal end, the channel; a window in mechanical communication with the monorail channel; a ramp; and a slot.

In some embodiments, the ramp may be disposed between the window and the monorail distal end at an angle to the central axis of the monorail tip. The ramp may be in mechanical communication with the monorail channel and/ or may be adapted to guide the distal end of the light guide outwardly from the central axis of the monorail tip as the distal end of the light guide is moved toward the monorail distal end. The slot may be disposed between the monorail distal end and the window. The slot may be in mechanical communication with the monorail channel and the window. The slot may be configured to permit a portion of the guidewire to move from within the monorail channel outwardly from the central axis of the monorail tip when the distal end of the light guide moves outwardly from the central axis of the monorail when engaged with the ramp.

In some embodiments, the monorail channel may include a distal monorail channel proximate to the monorail distal end, and sized to allow the guidewire to pass therethrough, and/or a proximal monorail channel proximate to the monorail proximal end, and sized to all the guidewire and the light guide to pass therethrough. In some embodiments, the guidewire may be eccentrically disposed within at least a portion of the light guide. In some embodiments, the slot width may be greater than the width of the guidewire and/or less than the width of the light guide. In some embodiments, a marker band may be disposed between the monorail distal end and the window.

In yet other embodiments a trigger may be coupled proximate with the elongated housing and the light guide. The trigger may be configured to actuate the light guide from a first position relative to the elongated housing to a second position relative to the elongated housing. In some embodiments, the trigger may be configured to actuate the light guide from the second position to the first position.

A catheter comprising an elongated housing, a fiber optic bundle, a monorail, a guidewire, and biasing means is provided according to another embodiment. The elongated housing may have a central axis, a distal end, a proximal end and a housing channel disposed between the distal end and the proximal end. The fiber optic bundle may include a distal end and a proximal end. The monorail may have a monorail distal end, a monorail proximal end, a central axis substantially parallel with the central axis of the elongated housing, and a monorail channel in mechanical communication with the housing channel extending from the monorail proximal end to the monorail distal end. The proximal end of the monorail may be mechanically coupled with the distal end of the housing channel. The guidewire may be at least partially disposed within the housing channel and at least partially disposed within the monorail channel. In some embodiments, a portion of the guidewire may exit the monorail through the monorail channel at the distal end of the of the monorail. In yet other embodiments, the guidewire may be in mechanical communication with the fiber optic bundle. The biasing means may be coupled with the monorail for biasing a portion of the fiber optic bundle proximal to the distal end of monorail at a position external to the monorail and substantially parallel with the central axis of the monorail.

A catheter may also include means for allowing the guidewire to extend from the distal end of the fiber optic bundle and exit the monorail through the monorail channel at the distal end of the monorail channel. The catheter may also include actuating means for actuating the distal end of the fiber optic bundle from a position within the monorail channel to a position external to the monorail in coordination with the biasing means.

A catheter comprising an elongated housing, a light guide, and a guidewire is provided according to another embodiment. According to this embodiment, the elongated housing may have a central axis, a housing distal end, a housing proximal end and a housing channel disposed between the distal end and the proximal end. The light guide may have a distal end and a proximal end and may be at least partially disposed within the housing channel. The guidewire may be at least partially disposed within the housing channel and in mechanical communication with the light guide and the elongated housing. The elongated housing may further include a window in communication with a portion of the housing channel. The elongated housing may also include a ramp disposed within the window at an angle to the central axis of the elongated housing that may be in communication with the housing channel and adapted to guide the distal end of the light guide outwardly from the central axis of the housing as the distal end of the light guide is moved toward the housing distal end. The elongated housing may also include a slot disposed between the housing distal end and the window. The slot may be in mechanical communication with the housing channel and the window and/or may be configured to permit a portion of the guidewire to move from within the housing channel outwardly from the central axis of the housing when the distal end of the light guide moves outwardly from the central axis of the housing when engaged with the ramp.

BRIEF DESCRIPTION OF THE DRAWINGS

The features and inventive aspects of the present invention will become more apparent upon reading the following detailed description, claims, and drawings, of which the following is a brief description.

FIG. 1 is perspective elevated view of a catheter according to one embodiment.

FIG. 2 is an exploded perspective view of a cavity of FIG. 1.

FIG. 3 is an exploded perspective view of FIG. 1 showing one embodiment of a ramp.

FIG. 4 is an exploded perspective view of FIG. 1 showing a ramp, a laser delivery member, and a guidewire.

DETAILED DESCRIPTION OF THE INVENTION

Figure 5:
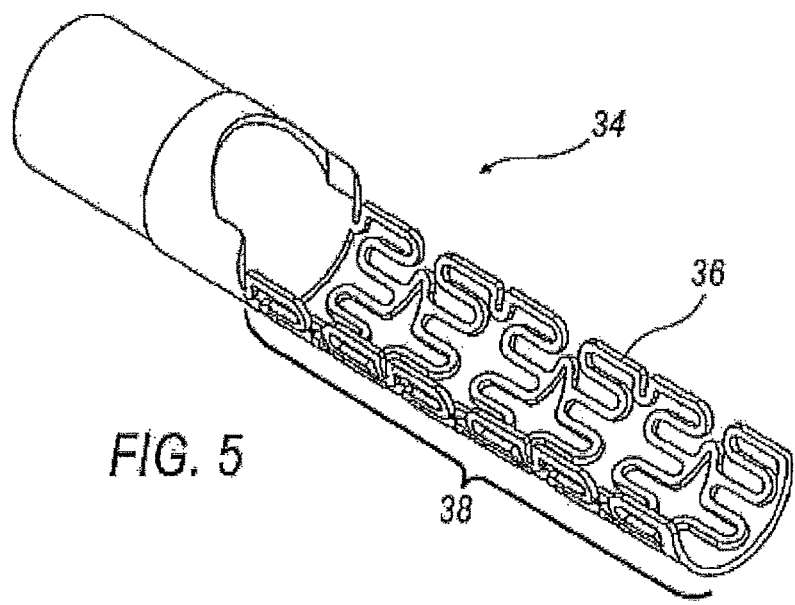
FIG. 5 is a perspective elevated view of a first embodiment of a support structure.

Referring now to the drawings, illustrative embodiments are shown in detail. Although the drawings represent some embodiments, the drawings are not necessarily to scale and certain features may be exaggerated to better illustrate and explain an innovative aspect of an embodiment. Further, the embodiments described herein are not intended to be exhaustive or otherwise limit or restrict the embodiments of the invention to the precise form and configuration shown in the drawings and disclosed in the following detailed description.

Referring now to FIGS. 1-4, a catheter 10 is shown having an elongated housing 12. The elongated housing 12 includes a central axis between a first proximal end 14 and a first distal end 16. A cavity 18 is located proximate to the first distal end 16 of elongated housing 12 having a ramp 20 at an angle to the central axis of the housing 12. The angle of the ramp 20 may but need not be the same over the length of the ramp. In some preferred embodiments, without limiting the scope of the invention, the housing includes a tapering end 30 and a guide wire aperture 32 capable of accepting the guidewire 28. A laser delivery member 22 comprising one or more optical fibers capable of transmitting light energy is disposed within a channel 26 of the housing 12 having a second proximal end (not shown) and a second distal end 24 movable therein. In some embodiments, without limitation, the laser delivery member 22 may be in mechanical communication with a guidewire 28 as further discussed below.

The guidewire 28 is threaded through a needle (not shown) into the artery and the needle is removed. The guidewire is advanced to or near the treatment site and may be inserted at its distal end into or across the lesion to be treated, as desired. The guidewire 28 serves as a tracking guide for the housing 12 and laser delivery member 22 to run on. Guidewires for such uses are known in the art and may comprise those with diameters between about 0.010 and 0.06 inches, with 0.014 and 0.018 inches diameter being typical sizes for artery applications. The guidewires may have bendable tips of coiled wire or plastic and a more rigid shaft of tapered ground stainless steel or other suitable material for push and torque transmission. The housing 12 and laser delivery member 22 are introduced coaxially, either sequentially or simultaneously, onto the guidewire 28 and advanced to a target area as further discussed below.

In some embodiments, without limitation, the housing 12 is introduced onto the guidewire 28 that has been inserted into the patient, and the housing is advanced to or near the treatment site such that portions of the guidewire 28 are disposed at least initially within the guide wire aperture 32, tapering end 30, and channel 26 of the housing. The laser delivery member 22 is then introduced onto the guidewire 28 so disposed within the catheter 10. The laser delivery member 22 is then advanced along the guidewire 28 such that the distal end 24 of the laser delivery member 22 becomes supported by the ramp 20 and oriented within the cavity 18 at any angle between 1 degree and 90 degrees in relation to the central axis of the housing 12, as desired by the user. Laser energy is then applied to the treatment site according to methods and protocols known to those of ordinary skill in the art. In some embodiments, without limiting the scope of the invention, in conjunction with the application of laser energy, the position of the laser delivery member 22 may optionally be varied by the user by moving the member 22 proximally or distally in order to adjust the angle of disposition of its distal end 24. Optionally, the offset of the central axis of the tip of the laser delivery member 22 from the central axis of the housing 12 may be varied by adjusting the distance that the delivery member 22 travels on the ramp 20 while keeping the central axis of the tip substantially parallel to the central axis of the housing 12. In addition, the catheter 10 containing the laser delivery member 22 may optionally be rotated along its central axis during the laser treatment and thereby apply laser energy to areas of the treatment site within the arc of the rotation. Optionally, the guidewire 28 may be withdrawn before application of laser energy and after the laser delivery member 22 has been introduced via the guidewire 28 into the channel 26 of the housing 12.

In some embodiments, the elongated housing 12 is an elongated structure having a lumen or channel 26 large enough to accommodate the laser delivery member 22 and guidewire 28. The channel 26 extends the entire length of the housing 12 from the first proximal end 14 to the first distal end 16. Optionally, in some embodiments, the channel 26 may extend only to the ramp 20. Various control mechanisms including electrical, optical, and mechanical control mechanisms may be employed with the housing 12 permitting the catheter to be specifically directed to a target area (not shown) within the blood vessel. One embodiment of the housing includes a tapering end 30 and a guide wire aperture 32 capable of accepting the guidewire 28. The housing 12 may be made from any rigid, semi-flexible, or flexible material including a combination thereof made from a material including metal, plastic, rubber, and the like. Round or flat metal ribbon wire may be embedded within the material, inserted through the cavity 18, or disposed at the first distal end 16 to add stability to the housing 12 at the first distal end 16. The length of the housing 12 may be varied as desired. The housing 12 may be one piece or have a plurality of sections including a support structure section at the first distal end 16 as discussed further below. The distal end 16 of the housing 12 may include a non-traumatic polymer tip separate or integrated into the housing 12. This allows the forces seen in bending to be dissipated throughout the structure, reducing stress risers that could cause failure. The housing 12 may also include at least one wire disposed within the channel 26 to add robustness to the housing 12. The channel 26 is in communication with cavity 18 and wire aperture 32. The channel 26 is open to the exterior of the housing 12 through the cavity 18.

The ramp 20 is disposed within cavity 18 and is configured to project the laser delivery member 22 outwardly at various determinable angles. Optionally, the ramp 20 is used to determine the offset of the central axis of the tip of the laser delivery member 22 from the central axis of the housing 20, while keeping the axis substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. In some embodiments, without limitation, the angle of lateral deviation of the ramp 20 from central axis of the housing 12 will vary in range as desired from one (1) degree to ninety (90) degrees, more usually in the range from thirty (30) degrees to sixty-five (65) degrees. By employing ramp 20 having different exit angles from the associated channel 26, different angles and/or offsets may be selected for treating a target area after the catheter 10 has been located within a patient. In some embodiments, without limitation, the ramp 20 may be adjustable, as one example only, by inflation of a balloon, and/or the ramp 20 may be slidable to allow varying degrees of offset.

The ramp 20 may be a built-up feature within the channel 26 of the housing 12 and may be located anywhere along the longitudinal length of the housing 12, but preferably at or within about 3 cm from the first distal end 16 of the housing 12. The ramp 20 may be formed or fused to the internal wall of the housing 12 and made from metal, plastic, rubber, and the like. In one embodiment, the ramp length (RL) is generally 1 cm. However, the ramp length (RL) may also be varied.

The first distal end 16 of the housing 12 may be formed from plastic, metal, or any combination thereof. When metal is used, materials must be selected to provide appropriate flexibility without producing failure since the cavity 18 tends to reduce the structural integrity of some portions of the housing 12. Thus, in some embodiments, the first distal end 16 comprises a shape memory alloy, as one example only, nickel-titanium alloy. In other embodiments, without limitation, the first distal end 16 may comprise a stent-like structure proximal, distal, within, or a combination of such proximate the cavity 18. The stent-like structure may be made from at least one of stainless steel, cobalt-chromium, nickel titanium, and the like.

Figure 6:
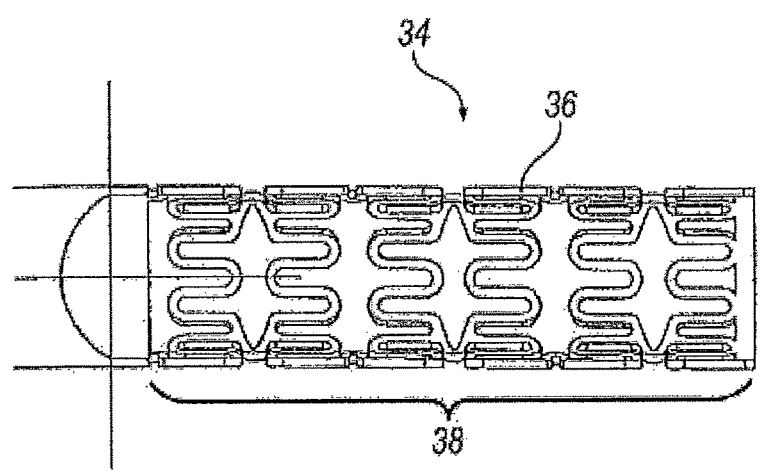
FIG. 6 is a top plan view of FIG. 5.
Figure 7:
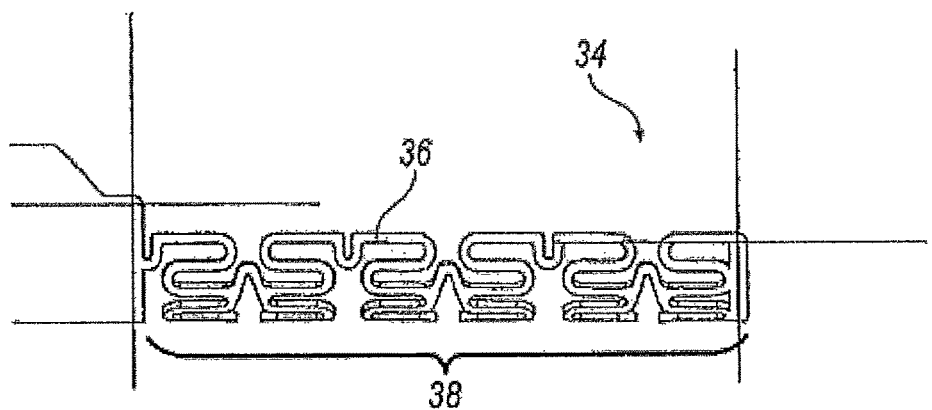
FIG. 7 is a side plan view of FIG. 5.

An alternative embodiment of the housing 12 comprises having at least one section at the first distal end 16. A first embodiment of a support structure is support member 34 as shown in FIGS. 5-7. The support member 34 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 34 assists in withstanding the torsional and bending forces when traversing bends of about 0.75 inches, while maintaining aspects of both integrity and functionality. In some embodiments, without limitation, support member 34 reinforces the area around the cavity 18 at the first distal end 16 with struts 36 forming a stent-like pattern 38. Support member 34 is formed from metal, plastic, or combinations thereof, and is at least partially axially disposed around the wall of the first distal end 16 of the housing 12. The housing 12 may be one longitudinal piece or have a plurality of sections including the support structure as described above disposed at the first distal end 16 of the housing 12. Other embodiments of the support structure include a marker band proximate the first distal end 16 of the housing 12 and radiopaque markers at various intervals along the ramp 20 to demarcate acceptable ramp 20 positions for the catheter 10. As one example only, a user may place a catheter at a first mark on the ramp to increase the offset for ablation to 1 mm. A second mark might equal a 1.5 mm offset. This way the support structure may be used progressively, as one example only, as a progressive atherectomy tool. Additional embodiments having generally similar benefits may also be used, as further discussed below.

Figure 8:
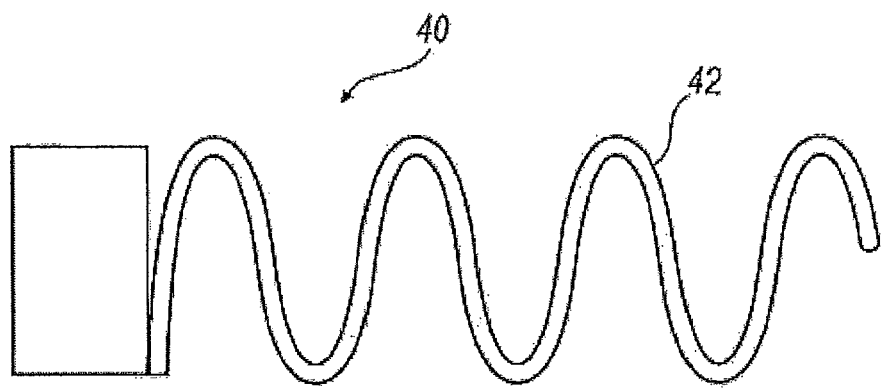
FIG. 8 is a top plan view of a second embodiment of a support structure.
Figure 9:
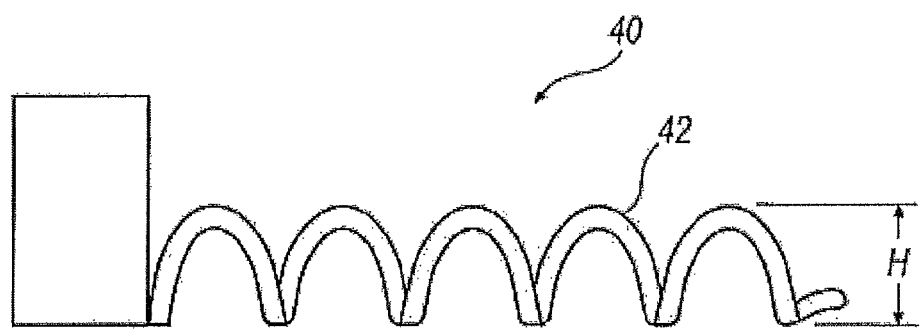
FIG. 9 is a side plan view of FIG. 8.

Referring to FIGS. 8 and 9, a second embodiment of a support structure is shown as second support member 40 having a spring-like geometry 42. The support member 40 may be used to support the first distal end 16 while providing flexibility without producing failure. The second support member 40 acts as a backbone for the first distal end 16 of the housing 12. The spring-like geometry 42 permits flexing without causing failure. The height H of the spring-like geometry 42 may be of any height but is preferably below the centerline of the second support member 40. The ramp 20 may be molded over the spring like geometry 42 including having a top coat (not shown).

Figure 10:
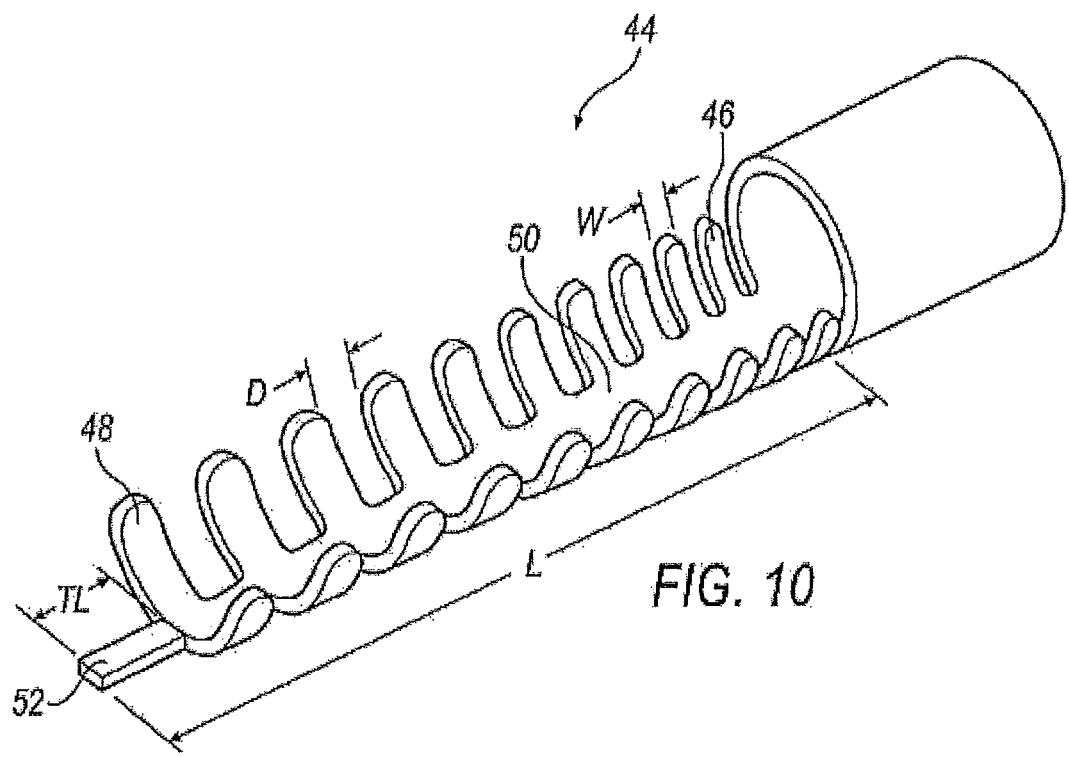
FIG. 10 is a perspective elevated view of a third embodiment of a support structure.
Figure 11:
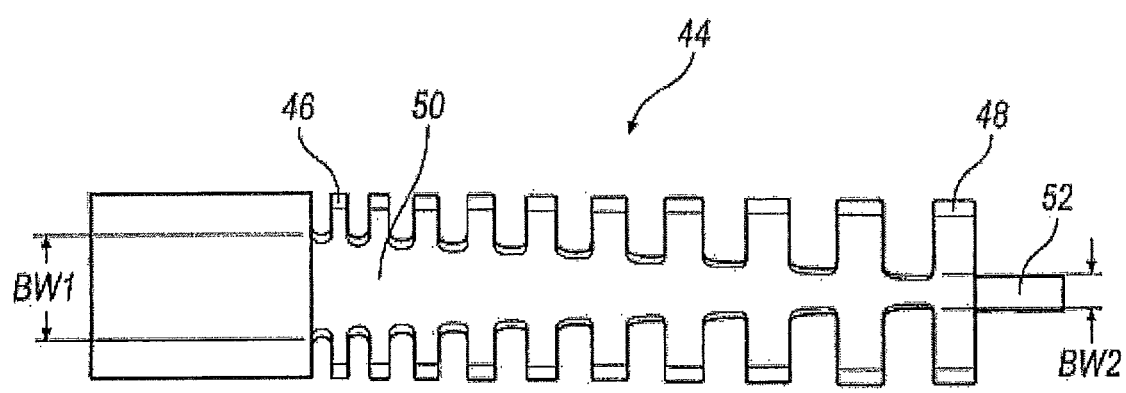
FIG. 11 is a top plan view of FIG. 10.

Referring to FIGS. 10 and 11, a third embodiment of a support structure is shown as a third support member 44. The support member 44 may be used to support the first distal end 16 while providing flexibility without producing failure. The third support member 44 provides variable stiffness along the length of the member 44. Member 44 is the most rigid at rib 46 and most flexible at rib 48. This flexibility is accomplished by having the ribs increase in width W and distance D in addition to decreasing the side of a beam 50 as shown in FIG. 11. Beam 50 tapers from a first wide beam width BW1 to a narrower beam width BW2. A tip 52 having a tip length TL disposed at the distal end support member 44 functions to provide support for the first distal end 16 of the housing 12 while allowing additional flexibility. The ramp 20 may be molded over the spring-like geometry 42 including having a top coat (not shown). The support member length L may be varied depending on user requirements including varying the tip length TL.

Figure 12:
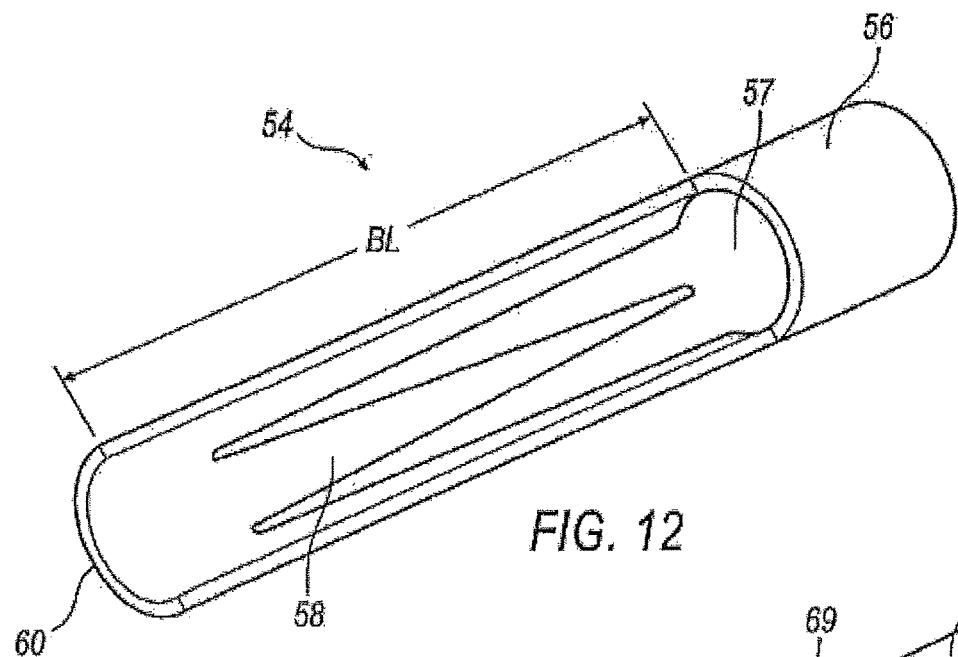
FIG. 12 is a perspective elevated view of a fourth embodiment of a support structure.

FIG. 12 shows a fourth embodiment of a support structure as fourth support member 54 disposed at the first distal end 16 of the housing 12. The support member 54 may be used to support the first distal end 16 while providing flexibility without producing failure. Support member 54 includes a rigid body 56 and a variably rigid base 58 extending from the body 56. Body 56 includes an aperture 57 in communication with channel 26. The base 58 may be elastomeric having the greatest flexibility at distal end 60. The ramp 20 may be molded over the base 58 including having a top coat (not shown). The support member base length BL may be varied according to user requirements.

Figure 13:
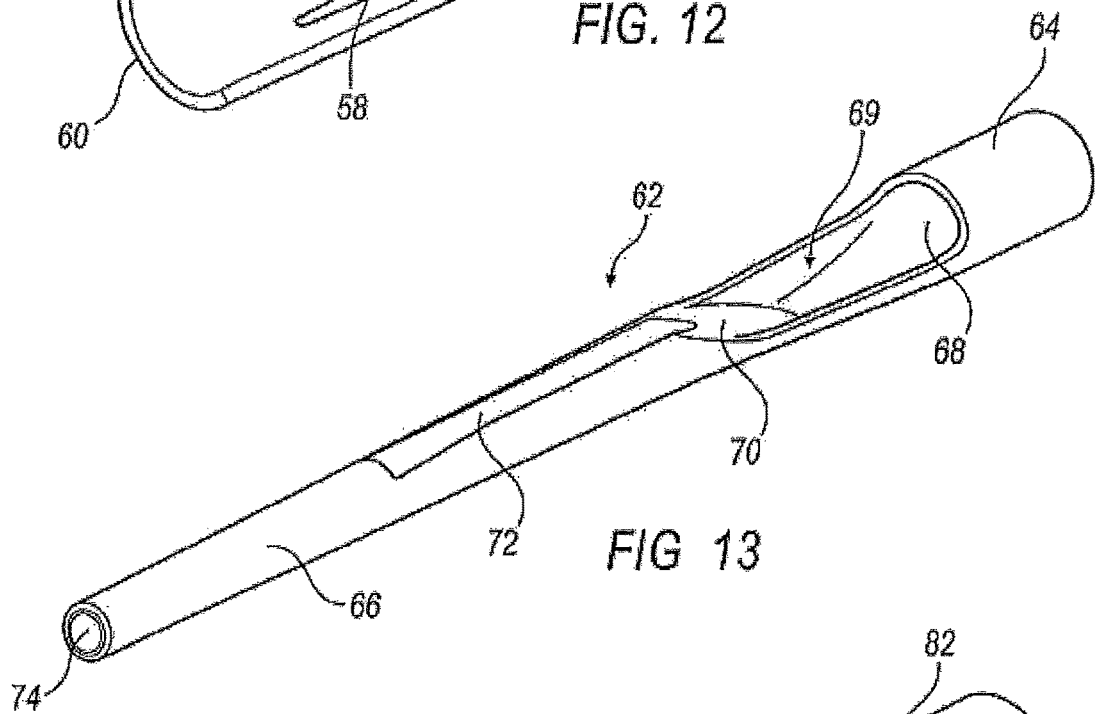
FIG. 13 is a perspective elevated view of a fifth embodiment of a support structure.

FIG. 13 shows a fifth embodiment of a support structure as fifth support member 62. The support member 62 includes a rigid body 64 having a flexible tapered nose portion 66. At least the nose portion 66 may be comprised of elastomeric material, as one example only, Rebax 55D available from Arkema. The body 64 is configured to communicate with the first distal end 16 of the housing 12. An aperture 68 is disposed within body 64 in communication with channel 26 of the housing 12 and is configured to accommodate both the laser delivery member 22 and guidewire 28. Aperture 68 is also in communication with the nose widow 69. The nose window 69 of the nose portion 66 includes a nose ramp 70 configured to project the laser delivery member 22 outwardly at various predetermined angles. Optionally, the ramp 20 is used to determine the offset of the central axis of the tip of the laser delivery member 22 from the central axis of the housing 20, while keeping the axes substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. Usually, the angle of lateral deviation of the ramp 20 from the housing 12 will vary in range as desired from one (1) degree to ninety (90) degrees, more usually in the range from thirty (30) degrees to sixty-five (65) degrees. The nose portion also includes a nose channel 72 and a nose guidewire aperture 74. The guidewire 28 disposed within and in mechanical communication the laser delivery member 22 extends outwardly from the second distal end 24 of the laser delivery member 22 and is guided through the nose channel 72 and extending out the guidewire aperture 74. Both the nose channel 72 and guidewire aperture 74 provide securement for the guidewire 28 so that the guidewire 28 may properly bias the second distal end N of the laser delivery member 22 generally inwardly toward the central axis of the body 64.

Figure 14:
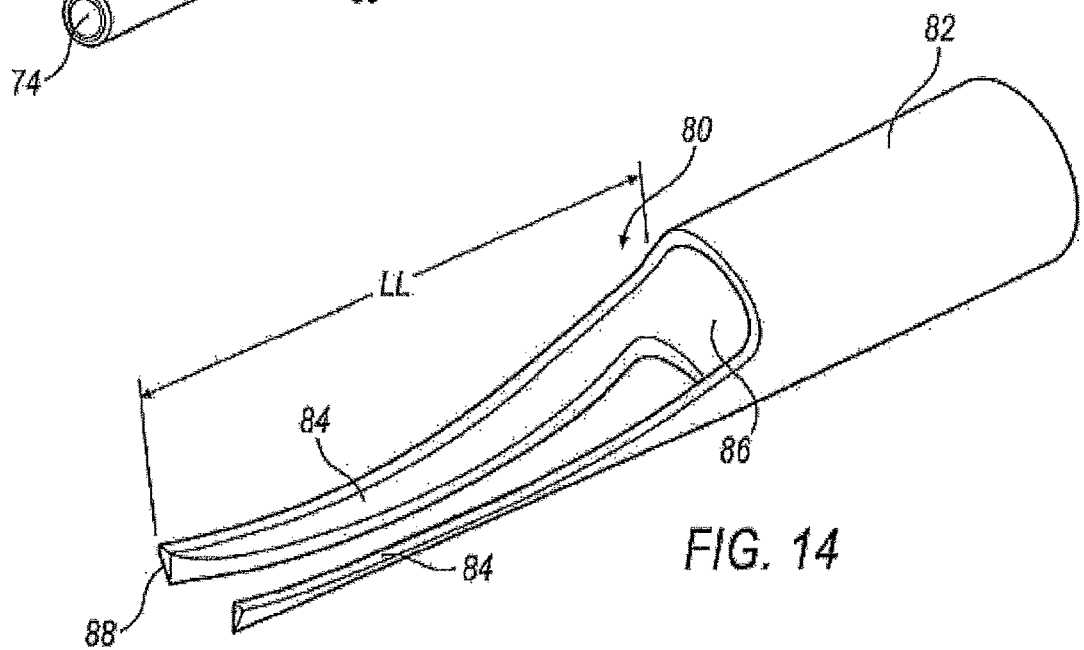
FIG. 14 is a perspective elevated view of a sixth embodiment of a support structure.

FIG. 14 shows a sixth embodiment of a support structure as sixth support member 80. The support member 80 may be used to support the first distal end 16 while providing flexibility without producing failure. Support member 80 includes a rigid body 82 and at least two variably rigid legs 84 extending from the body 82. Body 82 includes an aperture 86 in communication with the channel 26. The body 82 may be elastomeric having the greatest flexibility at distal end 88. The legs 84 may be of any shape extending from the body 82. The ramp 20 may be molded over the legs 84 including having a top coat (not shown). The support member leg length LL may be varied depending on user requirements.

Figure 15:
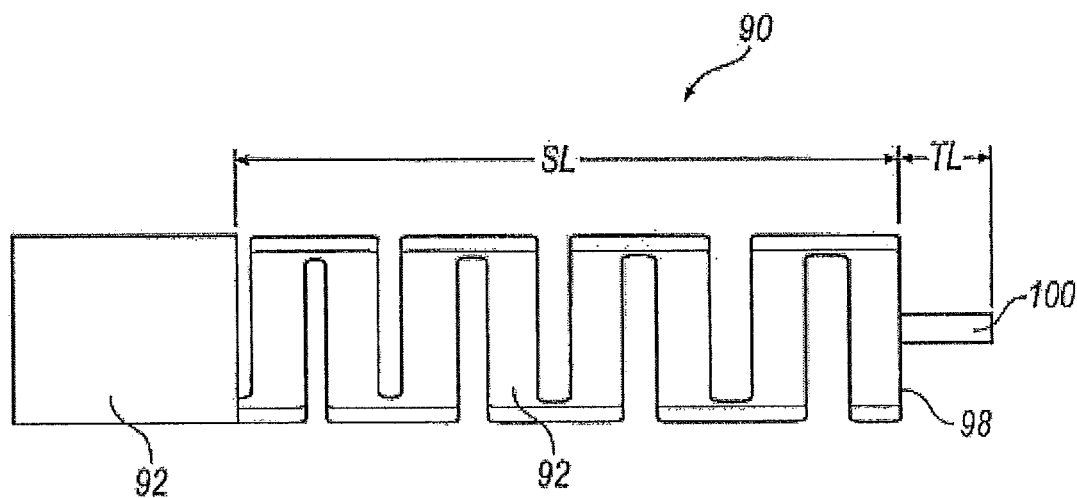
FIG. 15 is a top plan view of a seventh embodiment of a support structure.
Figure 16:
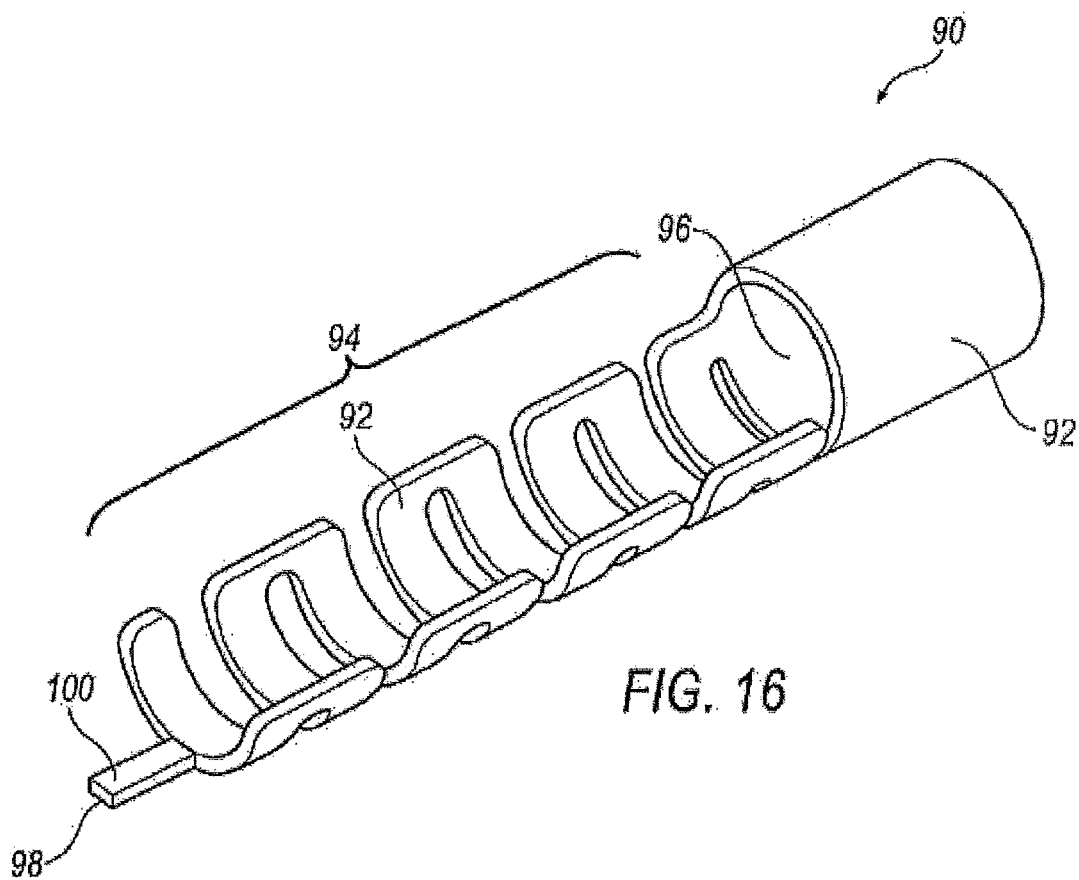
FIG. 16 is a perspective elevated view of FIG. 15.

FIGS. 15 and 16 show a seventh embodiment of a support structure as seventh support member 90. The support member 90 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 90 assists in withstanding the torsional and bending forces when traversing bends of about 0.75 inches while maintaining both integrity and functionality. Support member 90 reinforces the area around the cavity 18 at the first distal end 16 with a braid 92 forming a stent-like pattern 94. Support member 90 is formed from metal or plastic and is at least partially axially disposed around the wall of the first distal end 16 of the housing 12. The housing 12 may be one longitudinal piece or have a plurality of sections including the support structure as described above disposed at the first distal end 16 of the housing 12. Support member 90 includes a rigid body 92 and a variably rigid base 94 forming the stent-like pattern 94 extending from the body 92. Body 92 includes an aperture 96 in communication with channel 26. The base 94 may be elastomeric having the greatest flexibility at distal end 98. A tip 100 having a tip length TL disposed at the distal end support member 90 functions to provide support for the first distal end 16 of the housing 12 while allowing additional flexibility. The ramp 20 may be molded over the base 94 including having a top coat (not shown). The support member stent-like length SL may be varied depending on user requirements.

In operation, once the guidewire 28 is in place, or as it is being positioned, the housing 12 is inserted. This housing 12 has a central channel 26, which may include the laser delivery member 22 and guidewire 28. The housing 12 and the laser delivery member 22 are advanced through the guidewire into the desired target area. Therefore, the guidewire 28 is in mechanical communication with both the laser delivery member 22 and the elongated housing 12. However, the housing 12 may be advanced prior to inserting the laser delivery member 22. As the laser delivery member 22 approaches the ramp 20, it is biased in an outwardly direction through the cavity 18. The further the laser delivery member 22 is advanced, the more it projects outwardly from the cavity 18 at the first distal end 16 of the housing 12. In some embodiments, without limitation, the guidewire 28 disposed within the laser delivery member 22 biases the second distal end 24 of the laser delivery member 22 inwardly providing a travel path and forcing the second distal end 24 to face forward along the guidewire 28 and generally parallel to the centerline of the housing 12. Otherwise, the second distal end 24 of the laser delivery member 22 would continue along the ramp 20 further projecting away from the centerline of the housing 12 and would not be "attacking" the target area in front of the catheter 10 as desired.

FIGS. 17A, 17B, 18A, 18B, 19, 20, 21A, 21B, 22 and 23 provided examples of various other embodiments. Some of these embodiments may be related to one or more embodiments described above.

Figure 17A:
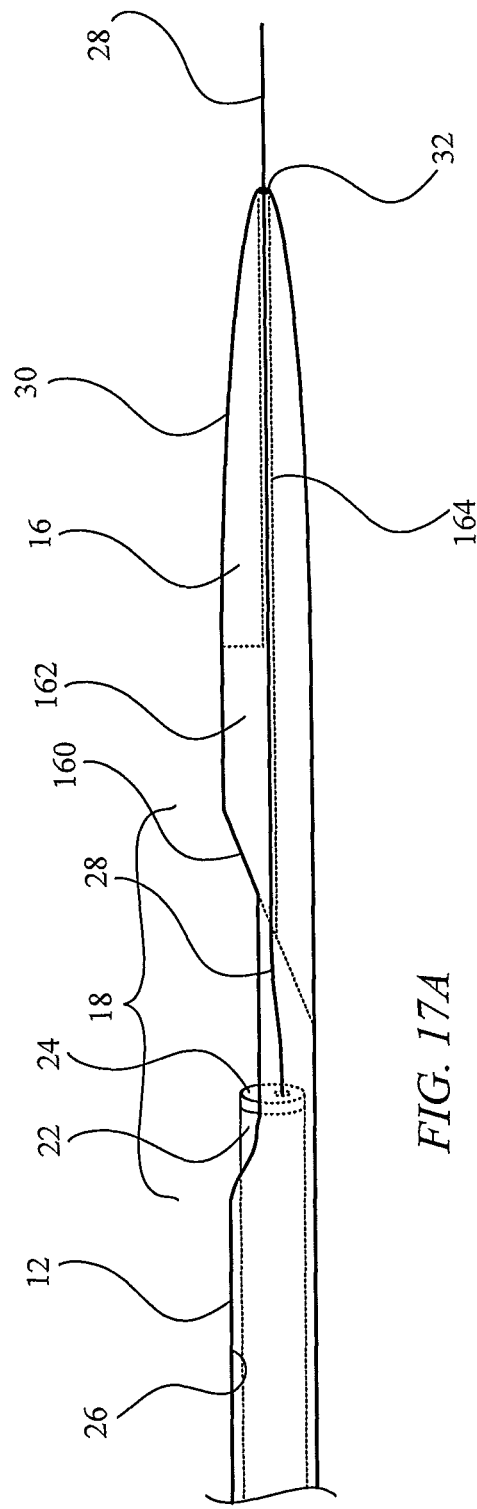
FIGS. 17A and 17B show top and side views of a laser catheter with a fiber optic bundle disposed within a window according to some embodiments.
Figure 17B:
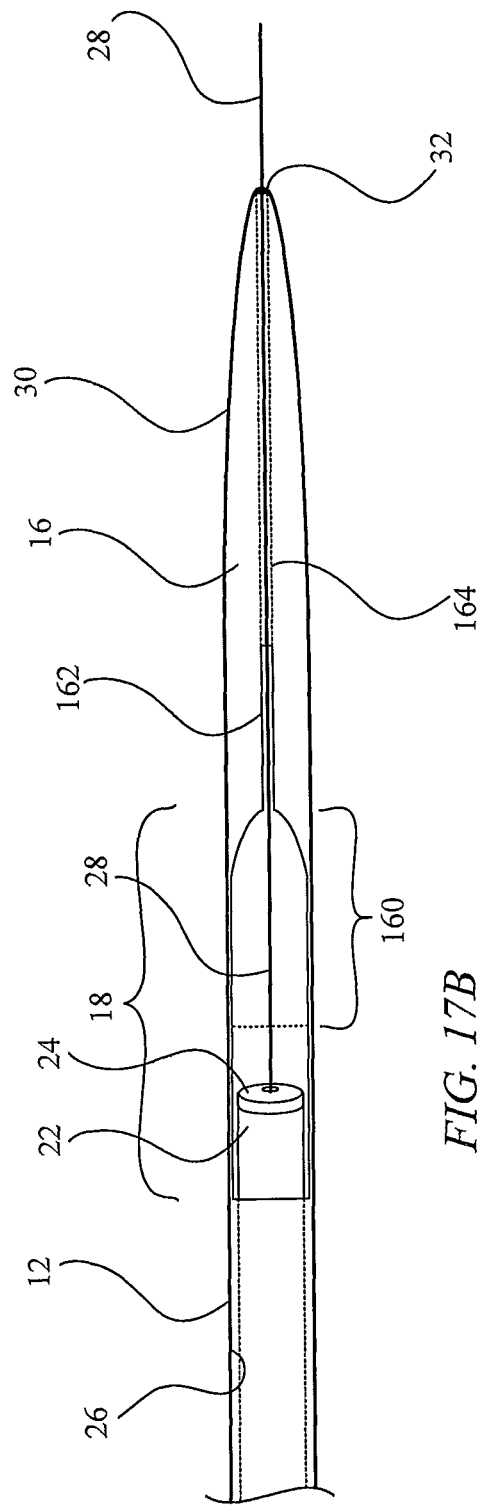
Figure 18A:
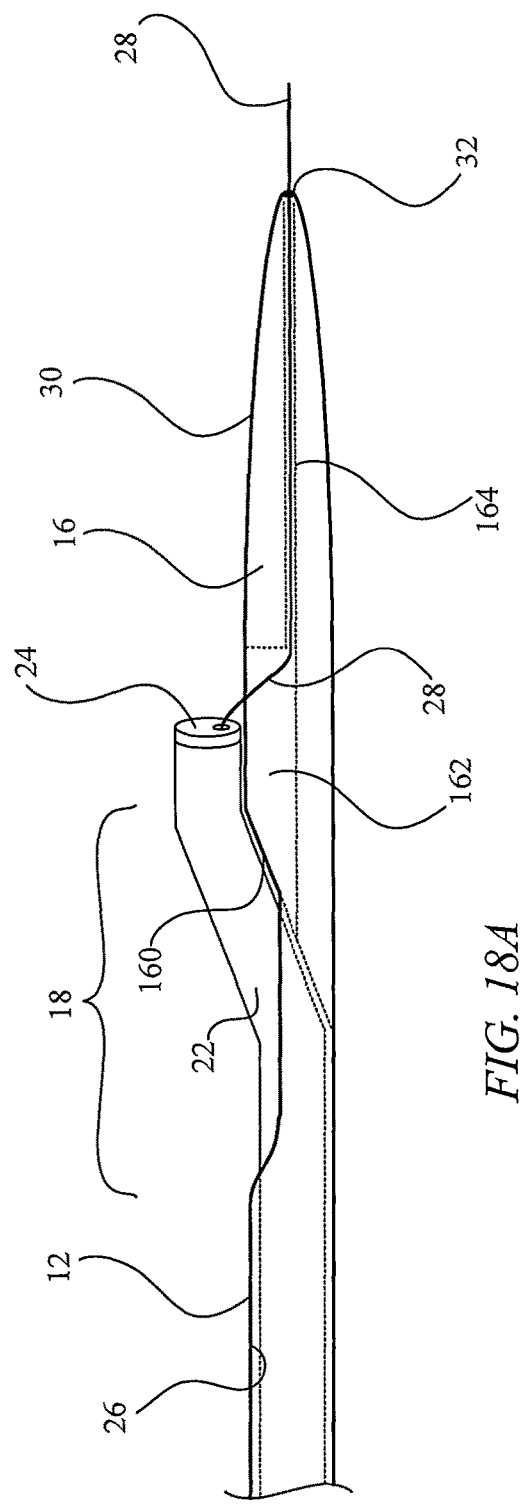
FIGS. 18A and 18B show top and side views of a laser catheter with a fiber optic bundle externally biased according to some embodiments.
Figure 18B:
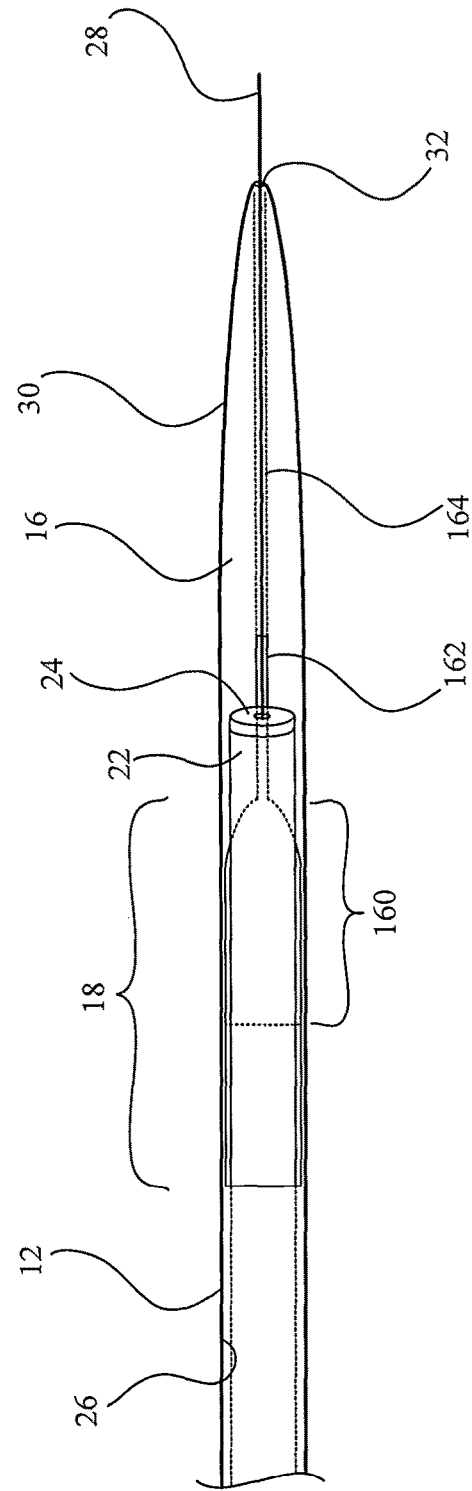

FIGS. 17A and 17B show top and side views of a catheter with fiber optic bundle 22 (laser delivery member or light guide) disposed within cavity 18 according to some embodiments. FIGS. 18A and 18B show top and side views of a catheter with fiber optic bundle 22 externally biased. The catheter include an elongated housing 12 with a fiber optic bundle (laser deliver member or light guide) 22 within the inner lumen 26 of the catheter. Fiber optic bundle 22, for, example, may include one or more optical fibers bundled within a sheath for the deliver of laser energy toward the distal end 24 of the fiber optic bundle. Elongated housing 12 may include a monorail tip 30 that may be an integral part of the elongated housing or a detachable tip according to some embodiments. The monorail tip 30 may include a cavity that exposes portions of the fiber optic bundle. The monorail tip 30 includes a monorail channel 164 that directs the guidewire from within the fiber optic bundle 22 toward an exit aperture 32 of the monorail tip 30. The monorail 30 tip may also in clued a ramp 160 and a slot 162. The ramp 160 may be integral with the monorail tip 30. The slot 162 may be mechanically connected with the monorail channel 164 and the cavity 18.

Figure 22:
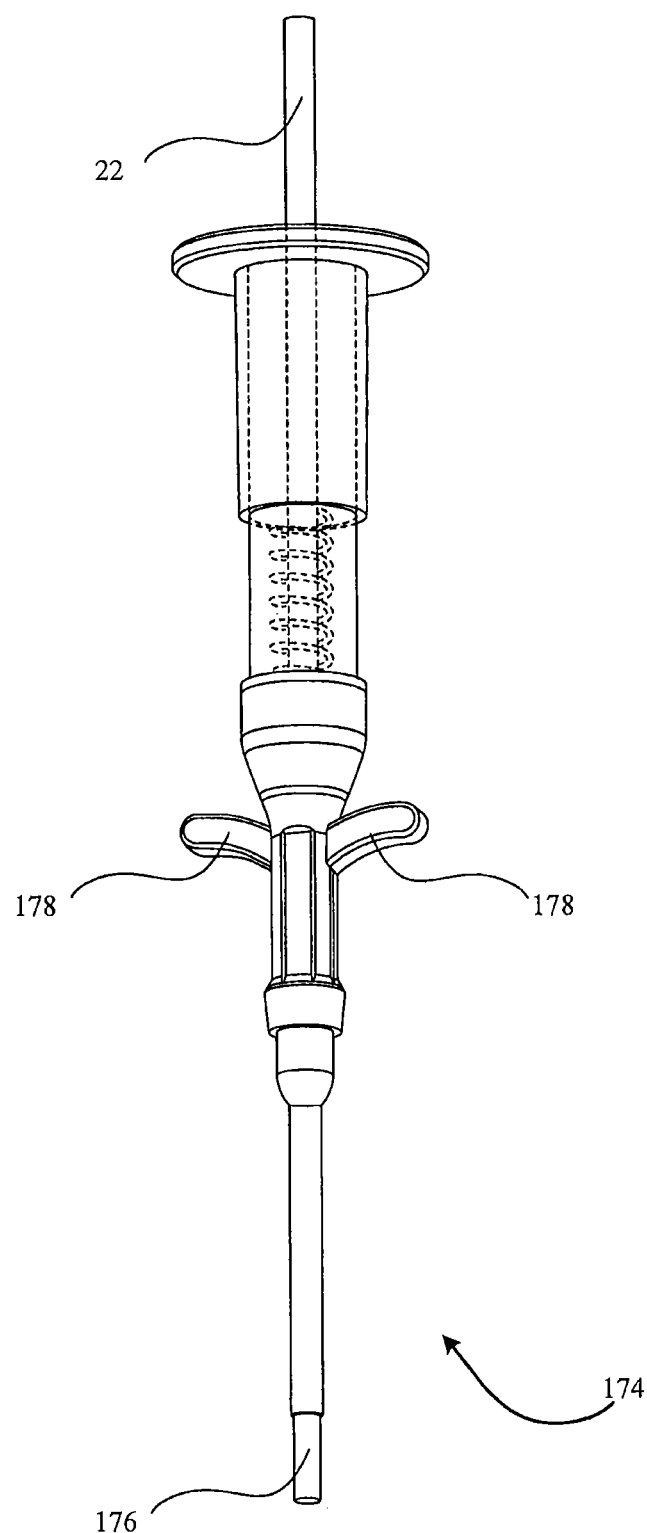
FIGS. 22A and 22B show examples of a trigger mechanism that may be employed at the proximal end of a laser catheter to actuate a fiber optic bundle within an elongated catheter body according to some embodiments.

Using an actuator, for example, an actuator like the one shown in FIG. 22, fiber optic bundle 22 may be moved from the position shown in FIGS. 17A and 17B to the position shown in FIGS. 18A and 18B. Looking at FIG. 17A, as fiber optic bundle 22 is linearly actuated within channel 26 of elongated housing 12, the distal end of fiber optic bundle 24 is engaged by ramp 160. As the distal end of fiber optic bundle 24 is actuated forward, the distal end 24 moves up the ramp 160. While distal end 24 moves up ramp 160, a portion of guidewire 28 moves from within channel 164 through slot 162. Ramp 160 may be linear or nonlinear. In some embodiments, ramp 160 has a steep slop, in other embodiments ramp 160 has a gradual slope. In some embodiments ramp 160 has a gradual curve in some positions and more steep curve in other portions. Slot 162 may also pass through ramp 160. Cavity 18 may comprise any size or shape and may be configured to permit the distal end of the fiber optic bundle to move from within cavity 18 as shown in FIGS. 17A and 17B up the ramp to the position shown in FIGS. 18A and 18B.

Monorail tips disclosed throughout this disclosure in various embodiments may be manufactured from plastic or metallic materials. Monorail tips may include, for example, one or more marker bands. For example, a marker band may be located near the distal end of the monorail tip. A marker band may also be located near the window or a monorail tip. If more than one marker band is used, the bands may have different widths or constructed with outer distinguishing features.

FIGS. 18A and 18B show the fiber optic bundle 22 at a resting position after actuation. In this position, for example, guidewire 28 biases distal end 24 toward the central axis of elongated housing 12. Guidewire 28, in this position, exits fiber optic bundle 22, passes through slot 162, passes through channel 164 and exits the elongated housing 12 through guide wire aperture 34. Slot 16 allows guidewire 28 to bias fiber optic bundle 22 toward the central axis of housing 12. FIG. 19 shows an example of an apparatus that may provide both channel 164 and slot 162.

FIGS. 17A, 17B, 18A and 18B also show examples of guidewire 28 positioned eccentrically within at least a portion of fiber optic bundle 22. For example, guidewire 28 may exit distal end 24 of the fiber optic bundle 22 from an off axis position. The eccentricity may decrease any optical dead area behind guidewire 28, which may result in increased light intensity from the fiber optic bundle 22.

The catheter tip may also include a separate monorail tip coupled with the elongated housing and the fiber optic bundle. The tip may be removable or non-removable. In some embodiments, the tip includes at least a ramp and a slot as described in regard to FIGS. 17A, 17B, 18A and 18B. In some embodiments, the monorail tip may include a window (or cavity), a proximal monorail channel for receiving the fiber optic bundle, and/or a distal monorail channel through which the guidewire may exit the monorail tip. In some embodiments, the monorail tip may be integral with the catheter.

As described above, the ramp 160 may be a built-up feature within the channel 26 of the housing 12 and may be located anywhere along the longitudinal length of the housing 12. For example, the ramp may be located within about 3 cm from the first distal end 16 of the housing 12. The ramp 20 may be formed or fused to the internal wall of the housing 12 and made from metal, plastic, rubber, and the like. In other embodiments, the ramp may be integrally formed as part of the walls of the housing. In one embodiment, the ramp length may be about 0.5 cm, 1 cm, 1.25 cm, 1.5 cm, etc. In other embodiments, the ramp may be located about 0.5 cm, 0.75 cm, 1 cm, 1.25 cm, 1.5 cm, 1.57 cm, 2 cm, 2.25 cm, 2.5 cm, etc from the distal end 16 of the housing 12.

The first distal end 16 of the housing 12 may be formed from plastic, metal, or any combination thereof. In some embodiments, the first distal end 16 of the housing may include a detachable monorail tip. In other embodiments, the first distal end of the housing 16 may include an integral monorail tip that is not detachable. When metal is used, materials must be selected to provide appropriate flexibility without producing failure since the cavity 18 tends to reduce the structural integrity of some portions of the housing 12. Thus, in some embodiments, the first distal end 16 may comprise a shape memory alloy, as one example only, nickel-titanium alloy.

FIG. 19 shows a biasing catheter with a guidewire introducer 150 according to some embodiments. Guidewire introducer 150 aids in introducing the guidewire within the catheter 12. In some applications, for example, a physician may guide the distal end of guidewire 28 into position with a patients arteries. Once in place, the proximal end of guidewire 28 may be thread into the catheter 12. The introducer may simplify the threading process. After used, the introducer 150 may be removed and possibly discarded. In other applications, for example, the introducer may be used prior to introducing the guidewire into the patient's arteries.

Figure 19A:
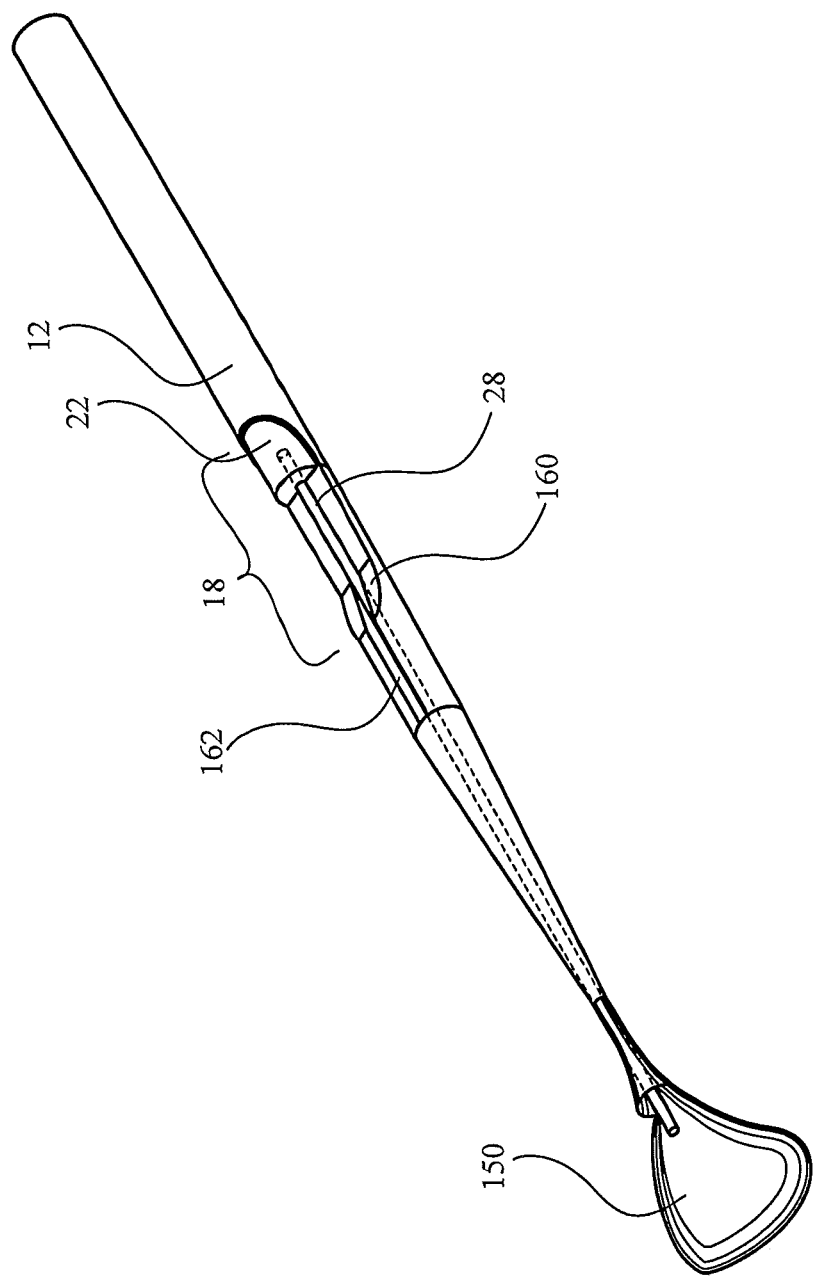
FIG. 19A shows a catheter with a monorail tip and a guidewire introducer according to another embodiment.

FIG. 19A also shows cavity 18 with ramp 160 disposed therein. Fiber optic bundle (light guide or laser delivery member) 22 in a first position may rest within cavity 18. After actuation, fiber optic bundle 22, for example, may move to a second position such that the distal end of fiber optic bundle 22 is disposed relative to the top of the ramp or beyond. In the second position, guidewire 22 biases the distal end of fiber optic bundle 22 back toward the elongated housing. As seen in FIG. 19, slot 162 is coupled with ramp 160. Moreover, a portion of slot 162 extends through ramp 160. At the distal end of ramp 160, the guidewire may continue through an internal cavity within the catheter and exit the catheter through the distal aperture and/or through the guidewire introduce 150. Guidewire introducer 150 may be used to guide a guidewire into the monorail tip, into the catheter and into the fiber optic bundle 22.

Figure 19B:
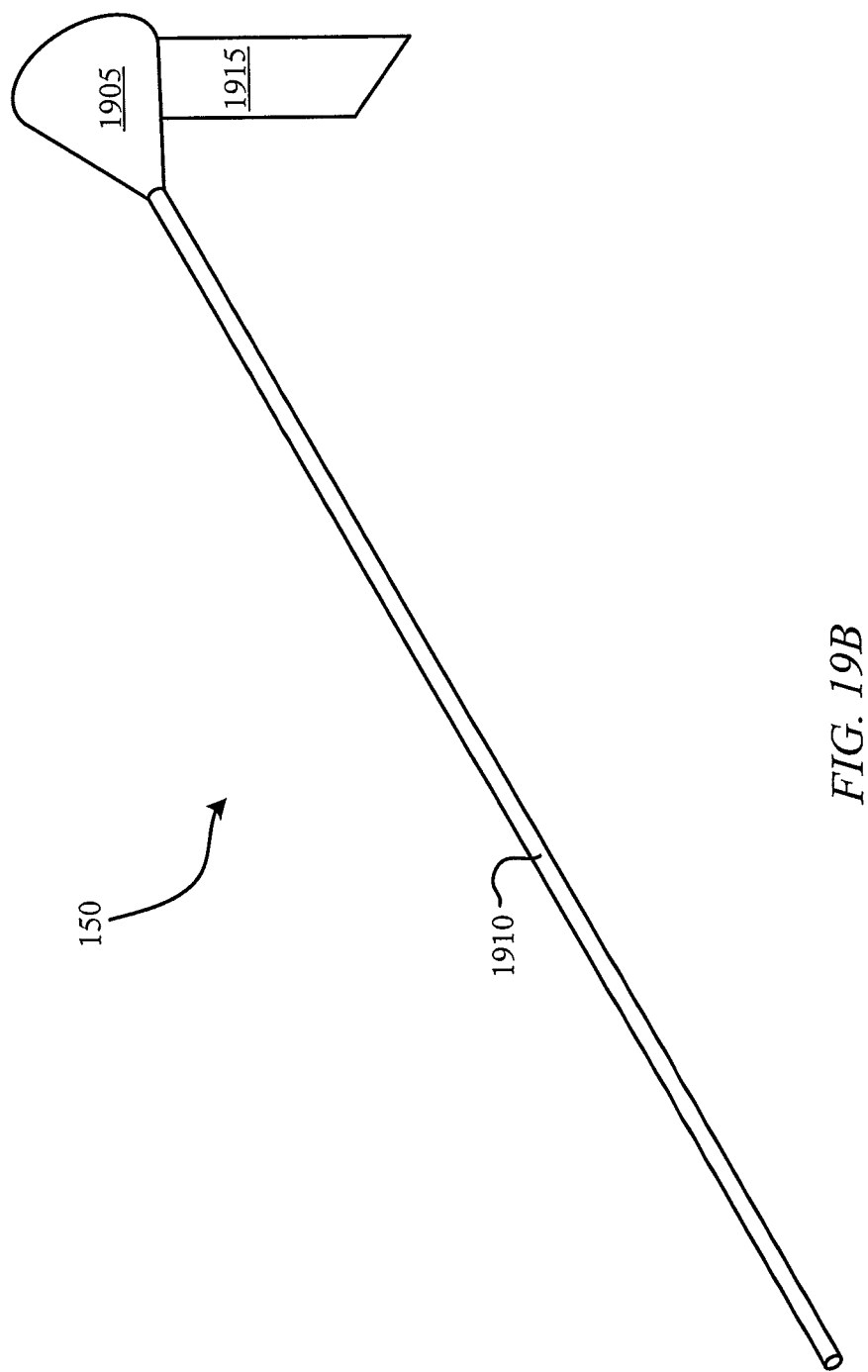
FIGS. 19B and 19C show different embodiments of a guidewire introducer according to some embodiments.
Figure 19C:
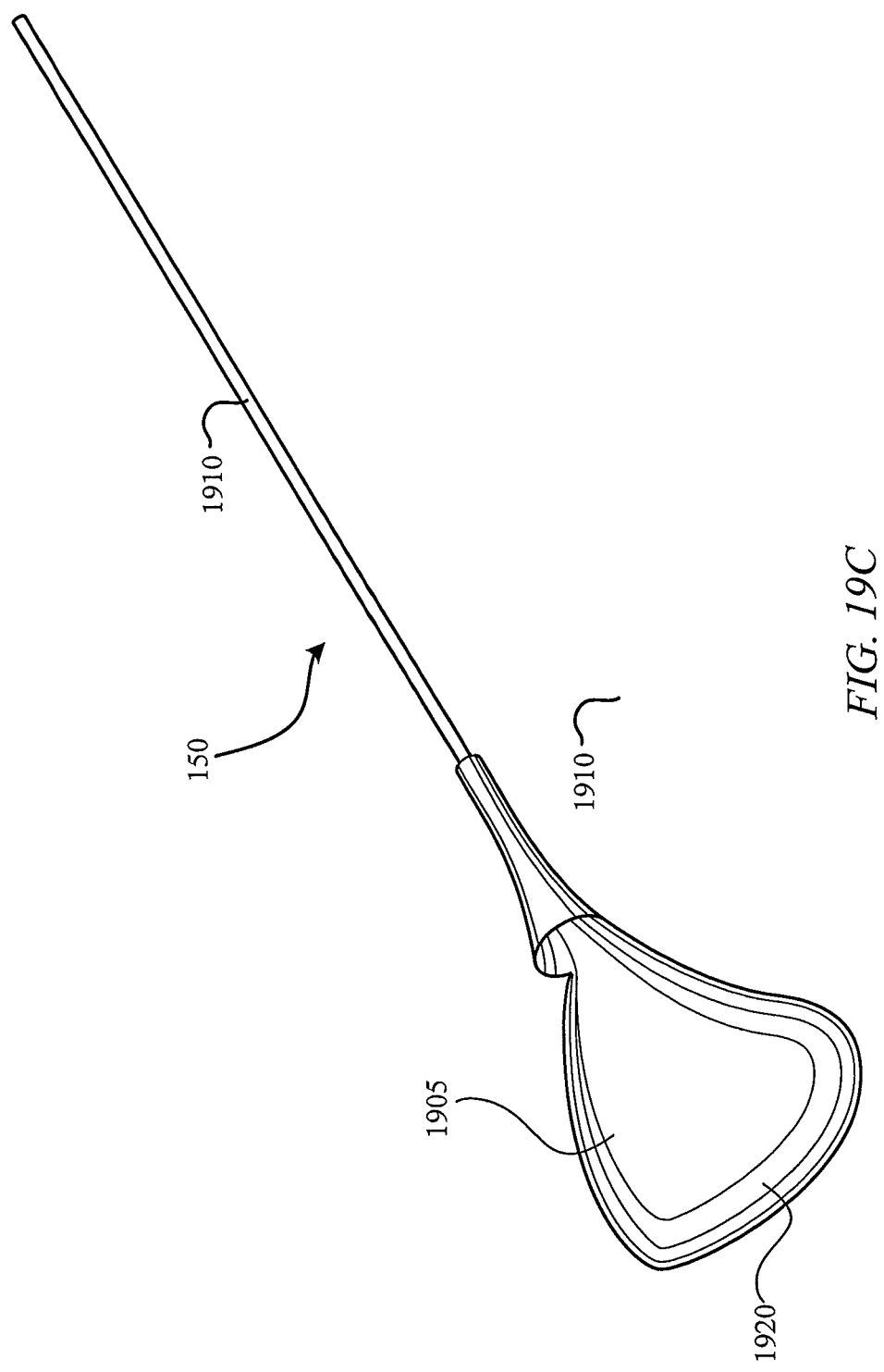

FIGS. 19B and 19C show exampled of guidewire introducers according to some embodiments. As shown in FIG. 19B, guidewire introducer includes a funnel section 1905, a thumb tab 1915, and elongated cylindrical section 1910. Elongated cylindrical section 1910 is coupled with funnel section 1905 and each have a channel (not shown) running through the length of the cylindrical section 1910 and the funnel section 1905. The channel is sized to allow a guidewire to pass there through. The funnel section 1910 may be used to slide a guidewire through the channel. The larger opening in the funnel section 1910 allows for simpler feeding of a guidewire therethrough. Once a guidewire is within the channel, the funnel section 1910 may be removed. The funnel section 1910 may include perforations or may be scored along a portion of the funnel to allow a user to remove the funnel while a guidewire extends through the channel. In some embodiments, the funnel section 1910 may be ripped, peeled, or pulled from the elongated section and the guidewire. In some embodiments, the body of the funnel section may be ripped or peeled such that the channel within the body of the funnel section may be exposed.

FIG. 19C shows another example of a guide wire introducer 150. In this embodiment, the thumb tab 1915 is not used. The funnel includes an extended section 1920 that may be used by a user to grip the funnel section 1905.

Figure 20:
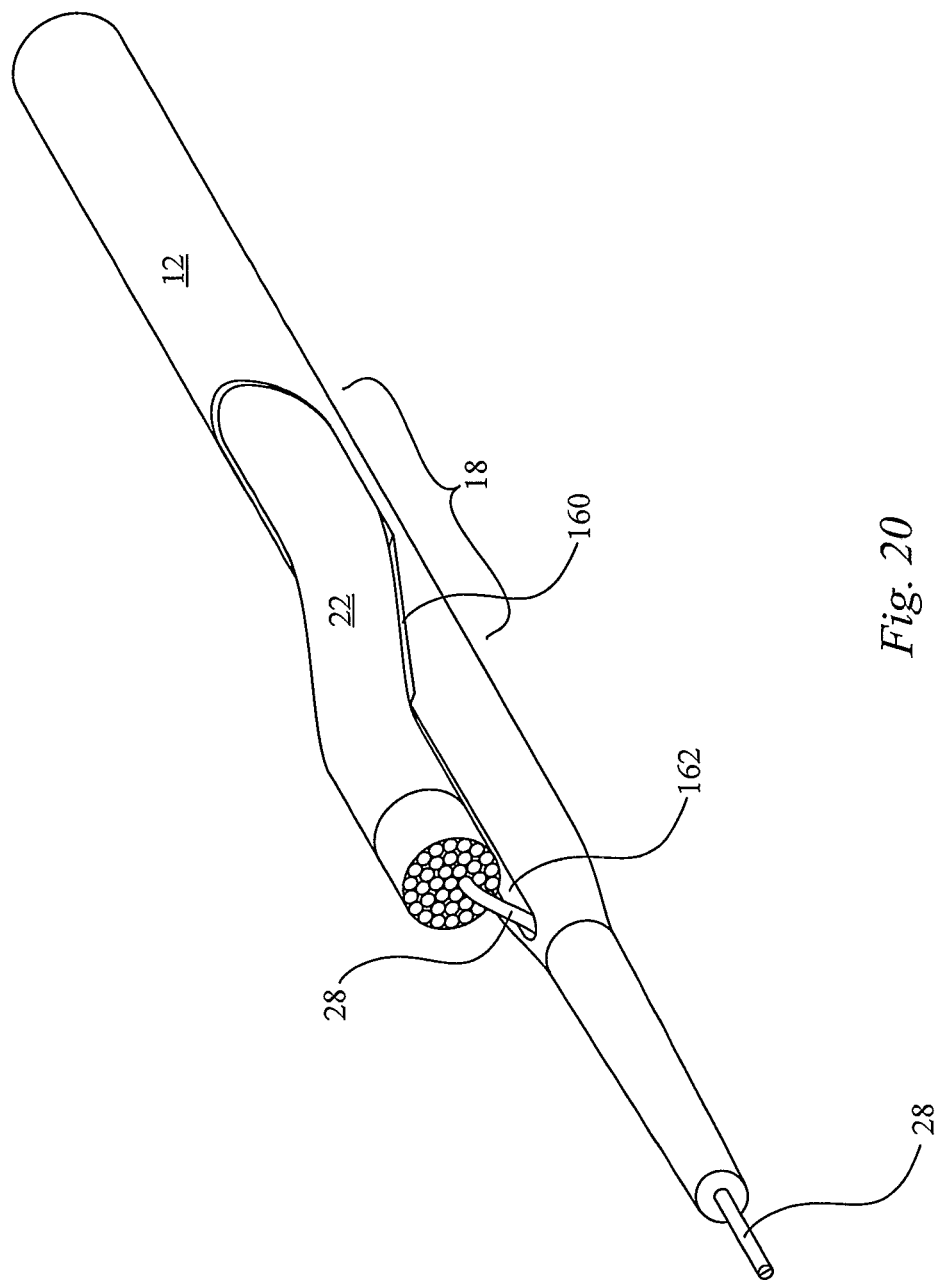
FIG. 20 shows a catheter with an externally biased fiber optic bundle according to some embodiments.
Figure 21B:
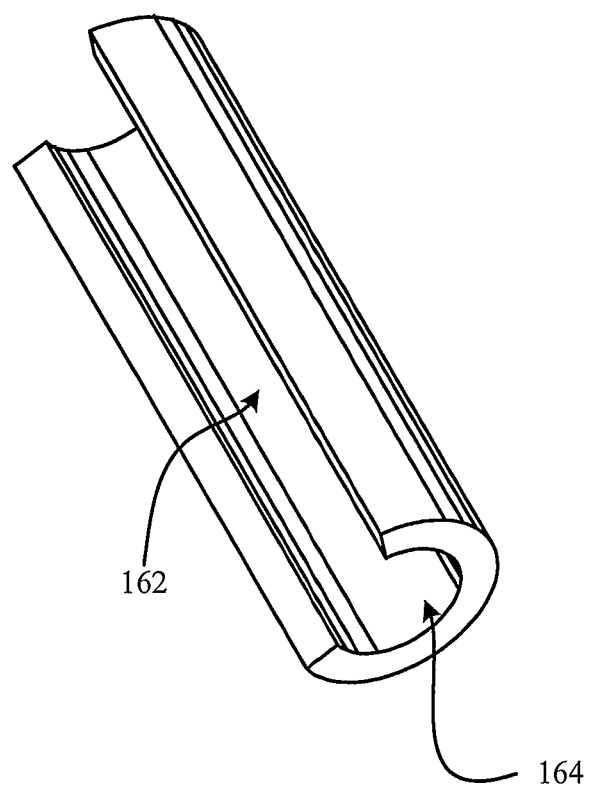
FIGS. 21A and 21B show portions of the monorail tip with cavity and a slot according to some embodiments.
Figure 21A:
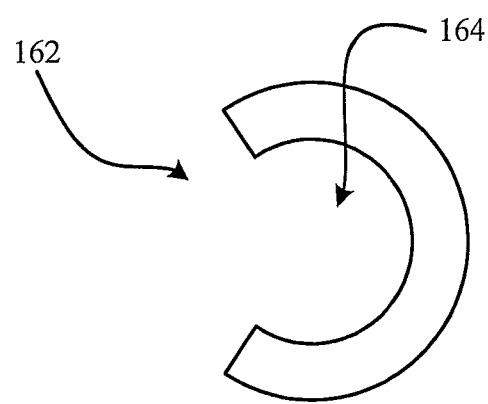

FIG. 20 shows a fiber optic bundle (light guide or laser delivery member) 22 in a second position outside the cavity 18 of the elongated housing 12. As shown, fiber optic bundle 22 is positioned near the outer surface of the catheter. Fiber optic bundle 22 may move from the first position shown in FIG. 19 to the second position shown in FIG. 20 by actuating fiber optic bundle 22 relative to the elongated housing 12.

During actuation, fiber optic bundle 22 is engaged with ramp 160 and may move to an exterior position as shown in FIG. 20. In the second position, the guidewire 28 enters the channel of the catheter through slot 162. Moreover, in some embodiments, guidewire 28 may also apply a biasing force to the fiber optic bundle 22 as it enters the slot and/or channel and may bias the distal end of the fiber optic bundle toward the central axis of the elongated housing 12.

FIG. 21 shows an example of a portion of the distal end of the catheter or of a monorail tip that may be used to provide a guidewire cavity and channel. As shown, slot 162 is proximate and part of channel 164. Various sizes of slot 162 and/or channel 164 may be used as long as a guidewire may pass through each. Moreover, slot 162 may have diameter smaller than the diameter of the fiber optic bundle used with the catheter to restrict entry through the slot only to the guidewire.

Figure 22B:
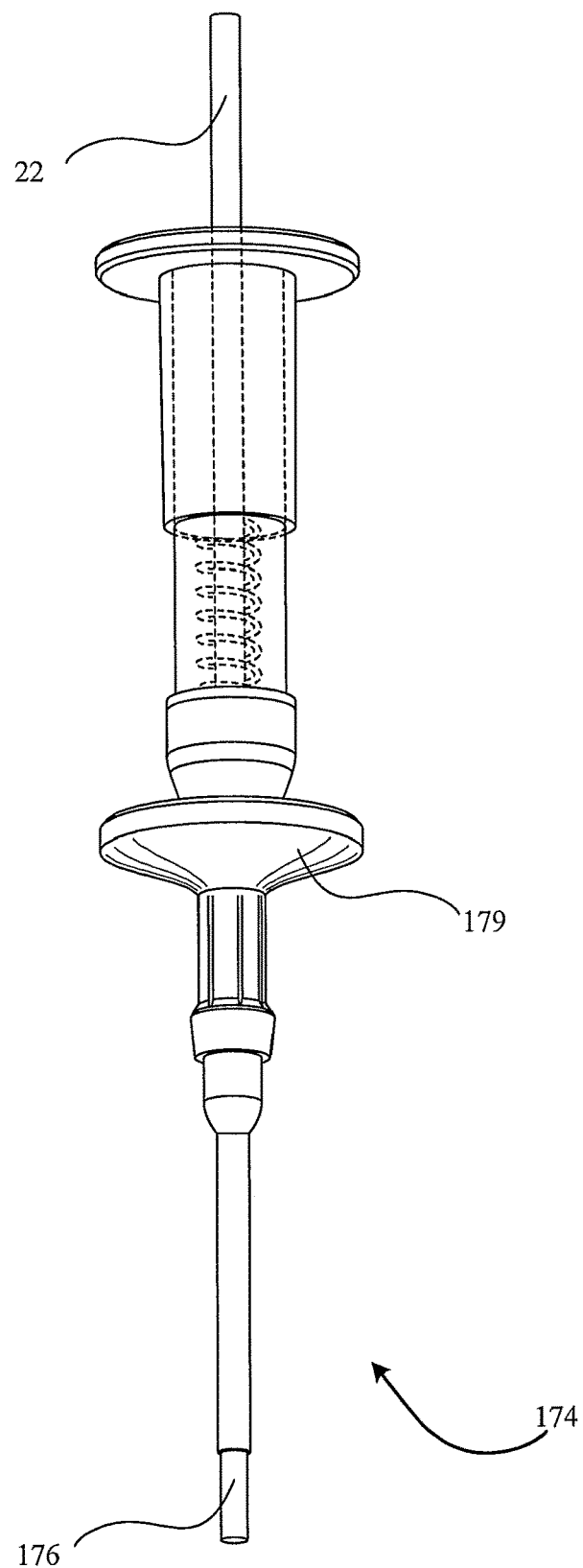

FIGS. 22A and 22B show examples of trigger mechanisms 174 according to some embodiments. Trigger mechanism 174 may be used to actuate a fiber optic bundle relative to an elongated housing. Such actuation may linearly advance the distal end of a fiber optic bundle from the first a position, for example, as shown in FIG. 19, to a second position, for example as shown in FIG. 20. The distal end of the trigger 176 may be coupled with an elongated catheter housing and a fiber optic bundle. The trigger, in some embodiments, may also provide a positive stop mechanism and/or a retraction mechanism. The trigger mechanism, for example, may linearly move the fiber optic bundle 1-2 cm relative to the elongated housing. In other embodiments, the trigger mechanism, for example may linearly move the fiber optic bundle 0.5 cm, 0.75 cm, 1 cm, 1.25 cm, 1.5 cm, 1.75 cm, 2 cm, 2.25 cm, 2.5 cm, 2.75 cm, 3 cm, and/or 3.25 cm, etc.

In some embodiments, trigger mechanism 174 linearly actuates the fiber optic bundle a fixed distance. Such a mechanism removes any guess work or subjectivity from manually actuating the fiber optic bundle without a trigger mechanism 174. In other embodiments, trigger mechanism 174 may have multiple stops. That is, the trigger mechanism may actuate the fiber optic bundle from a rest position to a first position. The trigger mechanism may then actuate the fiber optic bundle from the first position to a second position. From the second position the trigger mechanism may actuate the fiber optic bundle back to the rest position. In some embodiments, three, four, five, or more positions may be used. The trigger mechanism may require sequentially moving from one position to the next position. In another embodiment, the trigger mechanism may permit actuation from any position to any other position.

Trigger mechanism 174, may include one or more levers, buttons, and/or mechanical devices that may be used by a physician to actuate the fiber optic bundle. As shown in FIG. 22A, trigger mechanism 174 may include two handles 178 that may be gripped by the fingers. As handles 178 are moved upward relative to the rest of the trigger mechanism, the trigger mechanism 174 linearly actuates the fiber optic bundle. A second movement of handles 178, actuates the fiber optic bundle in an opposite direction causing the fiber optic bundle to return to the previous position. Trigger mechanism 174, in some embodiments, may employ springs that aide in returning the fiber optic bundle from the second position back to the first position. Moreover, various stop mechanisms may be employed. While a mechanical trigger mechanism is shown in the figures and described above, any other type of mechanism may be used. For example, a motor and/or pressure actuated trigger mechanism may be employed. In such examples, computer or electronic control may be used to control the trigger mechanism. FIG. 22B employs a disk that may be gripped by the fingers, rather than the handles shown in FIG. 22A.

As shown in FIG. 22, the fiber optic bundle 176 may pass directly through the trigger mechanism 174 and extend through the catheter.

Figure 23:
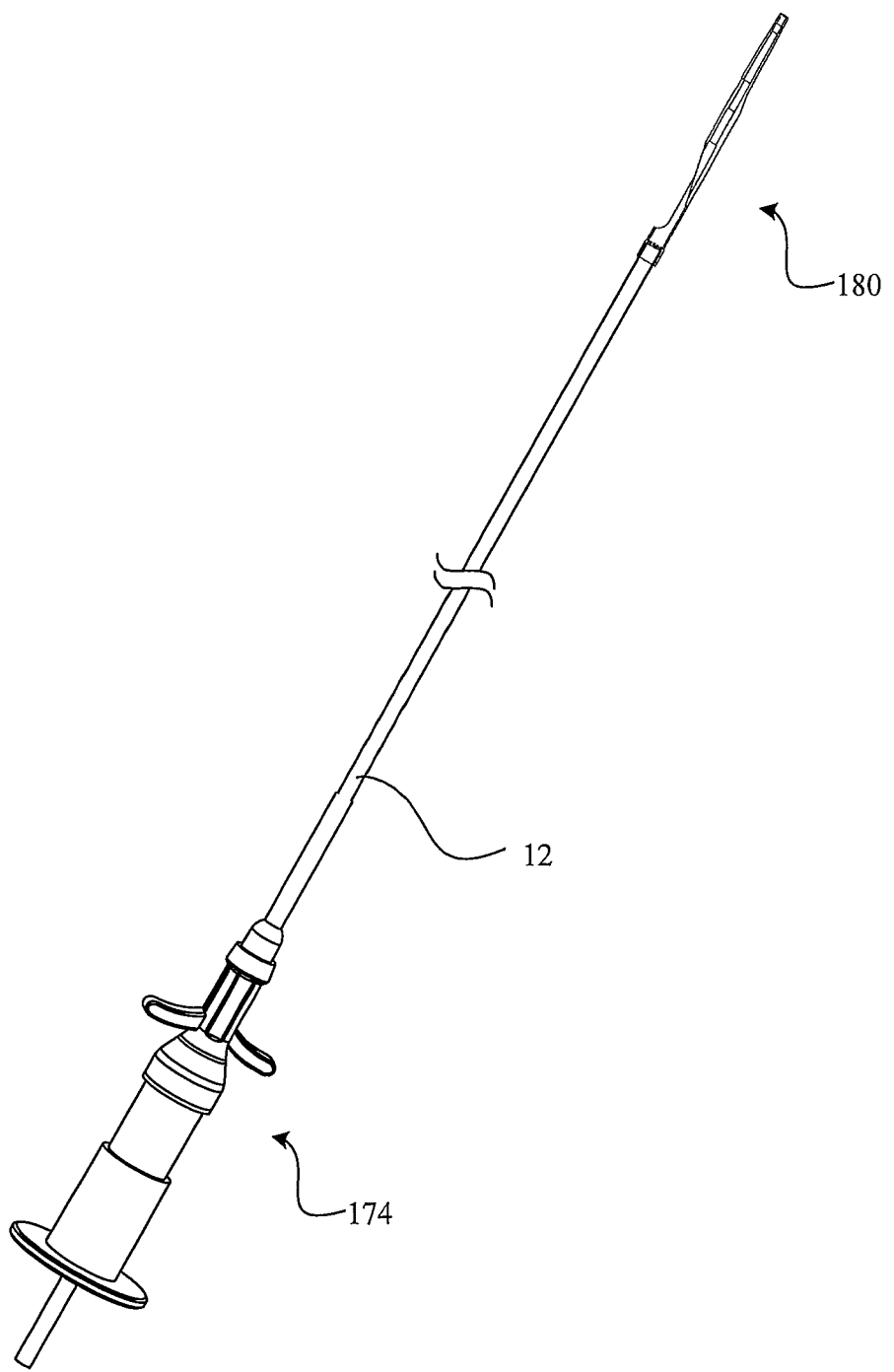
FIG. 23 shows a catheter with a monorail tip coupled with a trigger mechanism according to one embodiment.

FIG. 23 shows a trigger mechanism coupled with a catheter 12 that includes a monorail tip 180 according to one embodiment.

Figure 24A:
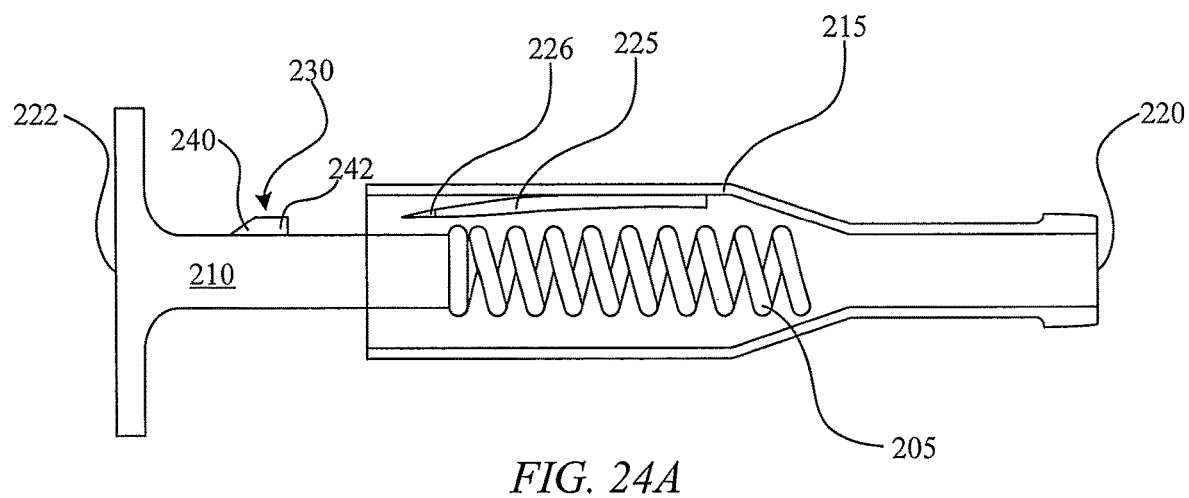
FIG. 24A-F show two views of a catheter lock-actuation mechanism in various positions according to some embodiments.
Figure 24B:
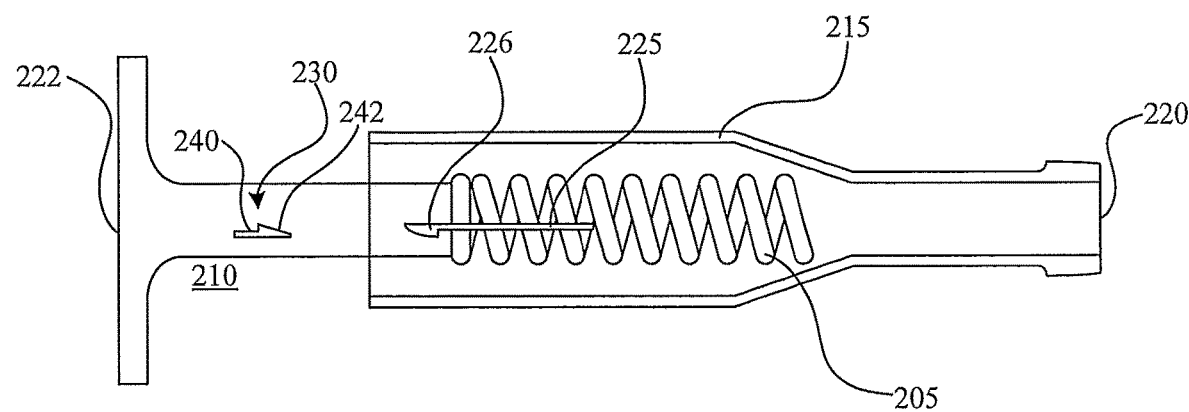

FIGS. 24A and 24B show a side and top view of an example of an internal trigger mechanism according to one embodiment. Various portions of a trigger mechanism are not shown in these figures solely for descriptive convenience. For example, finger grips are not shown. Plunger 210 is coupled with mechanism body 215. Plunger 210 extends into a portion of mechanism body 215 and is coupled with spring 205. A fiber optic cable and/or catheter may extend from the proximal end 222 of plunger 210 through mechanism 215 and exit through distal end 220 of mechanism body 215. Such a fiber optic bundle or catheter may be coupled with plunger 210 and/or slide through mechanism 215. An engagement arm 225 with tip 226 is located within mechanism 215. A catch block 230 is coupled with part of plunger 210. Catch block 230 includes a front end 242 and a back end 240. Engagement arm 225 and catch block 230 work in harmony to provide stop actuation to a fiber optic and/or catheter coupled with plunger 210.

Figure 24C:
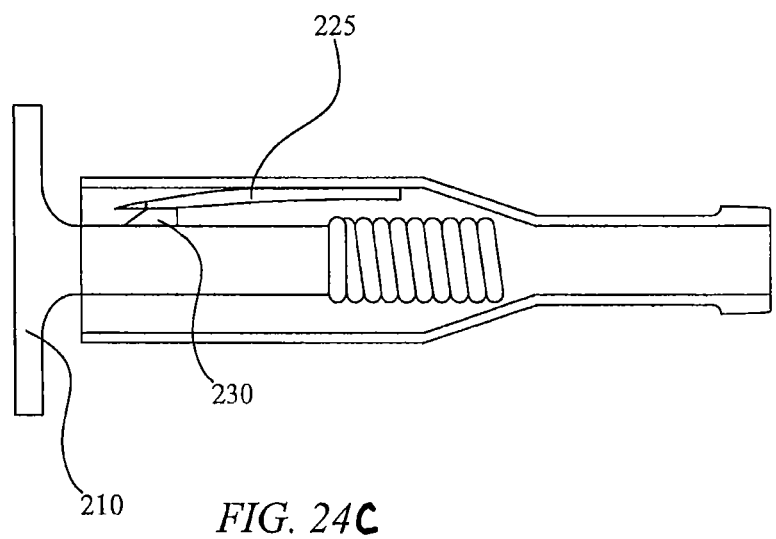
Figure 24D:
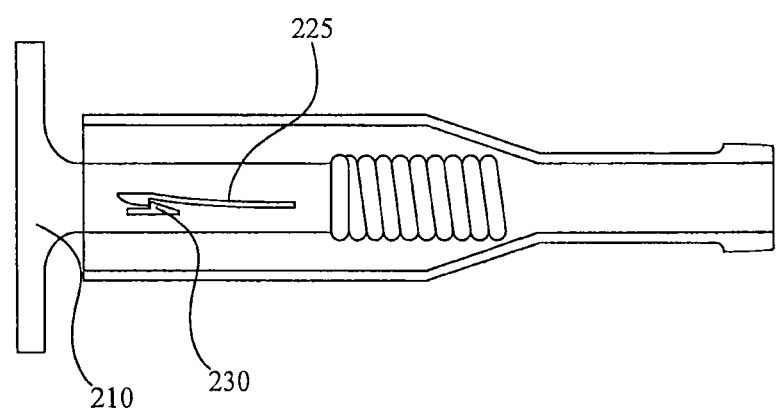
Figure 24E:
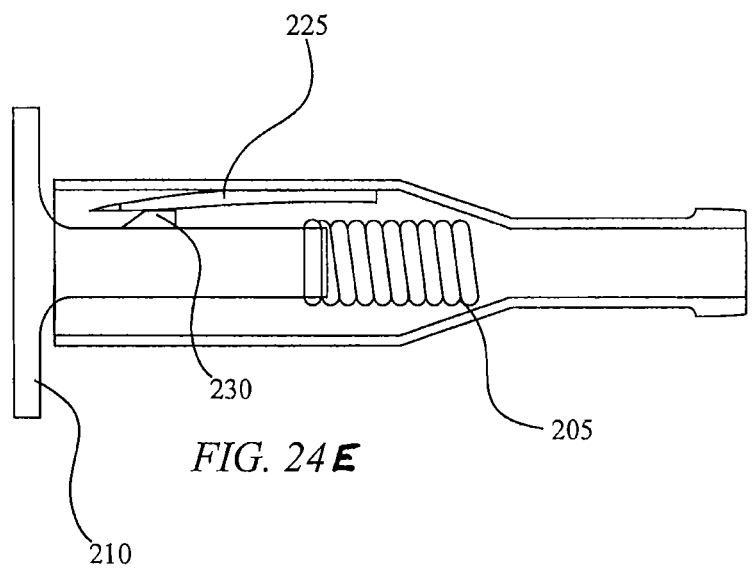
Figure 24F:
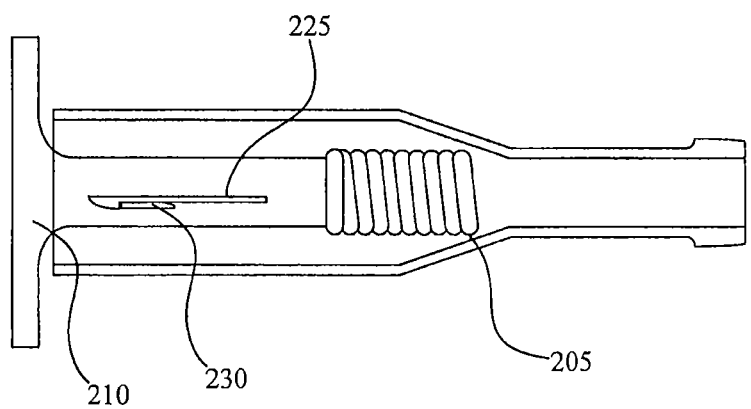

As plunger 210 is pressed toward mechanism body 215 by a user, engagement arm 225 contacts the front end 242 of catch block 230. Engagement arm 225 becomes biased and locks with catch block 230 as shown in FIGS. 24C and 24D. Once in this position, plunger 210 may rest at this actuated position. When plunger 210 is pressed again, engagement arm 225 moves passed catch block 230 as shown in FIGS. 24E and 24F. Once past catch block 230, when pressure on plunger 210 is released by the user, spring 205 pushes the plunger back out. Engagement arm 225 slides over the top of catch block 230. The internal trigger mechanism may then return to the position shown in FIGS. 24A and 24B.

Various other trigger mechanisms may also be used. For example, the engagement arm may be coupled with the plunger and the catch block may be coupled with the mechanism body. A similar action may lock and/or actuate the plunger relative to the mechanism body. Various other engagement arms and catch blocks may be employed.

The lock-actuation mechanism described above and shown in FIGS. 24A-24F may be used to actuate a fiber optic bundle through a catheter body. The plunger, for example, may be coupled with the fiber optic bundle and the mechanism body may be coupled with the catheter body. Thus, the actuation and/or locking discussed above, may actuate and/or lock a fiber optic bundle relative to the catheter body.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A catheter for insertion into a vasculature of a patient, the catheter comprising:
    an elongated housing having a first proximal end, a first distal end, a central axis, a housing channel disposed between the first proximal end and the first distal end, and a cavity disposed proximate the first distal end of the elongated housing and in communication with the housing channel;
    a monorail tip detachably coupled to the first distal end of the elongated housing, the monorail tip comprising:
        a first guidewire channel in communication with the housing channel;
        a ramp disposed within the first guidewire channel of the monorail tip at an angle to a central axis of the monorail tip; and
        a slot exposing at least a portion of the guidewire channel adjacent to the ramp to the vasculature of the patient;
    a laser delivery member having a second proximal end, a second distal end, at least one optical fiber, and a second guidewire channel, the laser delivery member being at least partially disposed within the housing channel and movable therein to the first guidewire channel of the monorail tip; and
    a trigger mechanism coupled to the elongated housing and the laser delivery member, the trigger mechanism having a body and a plunger disposed at least partially within the body, whereupon pressure applied to the plunger distally and longitudinally advances the laser delivery member by a fixed distance through the housing channel of the elongated housing to the guidewire channel of the monorail tip;
    wherein the trigger mechanism further comprises an engagement arm coupled to the body and a catching device coupled to the plunger, wherein the catching device comprises a plurality of stops, whereupon coupling of the engagement arm into one of the stops of the catching device locks the laser delivery member relative to the elongated housing; and
    wherein actuating of the trigger mechanism advances the engagement arm to couple with the different stops of the block so that the second distal end of the laser delivery member engages the ramp in the monorail tip and moves outwardly and laterally away from the central axis of the monorail tip to orient the at least one optical fiber at a non-zero angle away from the central axis of the monorail tip and to thereby permit ablation of a target area that is larger than the distal end of the catheter.

2. The catheter according to claim 1, whereupon distally and longitudinally advancing the plunger, in cooperation with a guidewire in communication with the first guidewire channel, the second guidewire channel and the slot, the second distal end of the laser delivery member moves toward a position parallel with the central axis of the elongated housing.

3. The catheter according to claim 1, wherein the trigger mechanism further comprises a second catching device coupled to the plunger.

4. The catheter according to claim 1, wherein the trigger mechanism further comprises a spring that applies a longitudinal force on the plunger in a distal direction, such that upon decoupling the engagement arm and the catching device, the plunger moves proximally.

5. The catheter according to claim 1, wherein the trigger mechanism further comprises a spring that applies a longitudinal force on the plunger in a proximal direction, such that upon decoupling the engagement arm and the catching device, the laser delivery member returns to an unlocked position relative to the monorail tip.

6. The catheter according to claim 1, wherein the monorail tip further comprises at least one radiopaque marker.

7. The catheter according to claim 6, wherein the at least one radiopaque marker is located on the first distal end of the monorail tip.

8. The catheter according to claim 1 wherein the ramp has a varying slope corresponding to a plurality of different non-zero orientation angles of the optical fiber relative to the central axis of the monorail tip.

* * * * *